(12) United States Patent
Merino-Lopez et al.

(10) Patent No.: US 7,404,318 B2
(45) Date of Patent: Jul. 29, 2008

(54) MEASUREMENT OF ADHERENCE BETWEEN A VEHICLE WHEEL AND THE ROADWAY

(75) Inventors: Jose Merino-Lopez, Riom (FR); Pierrick Travert, Beaumont (FR); Jean-Francois Parmentier, Clermont-Ferrand (FR)

(73) Assignee: Michelin Recherche et Technique S.A., Granges-Paccot (CH)

( * ) Notice: Subject to any disclaimer, the term of this patent is extended or adjusted under 35 U.S.C. 154(b) by 0 days.

(21) Appl. No.: 11/828,801

(22) Filed: Jul. 26, 2007

(65) Prior Publication Data

US 2008/0016955 A1 Jan. 24, 2008

Related U.S. Application Data

(60) Division of application No. 10/071,135, filed on Feb. 6, 2002, now Pat. No. 7,267,148, which is a continuation-in-part of application No. 09/636,566, filed on Aug. 10, 2000, now abandoned.

(30) Foreign Application Priority Data

| Aug. 10, 1999 | (FR) | ................................. 99 10422 |
| Dec. 31, 1999 | (FR) | ................................. 99 16835 |
| Feb. 7, 2001 | (FR) | ................................. 01 01672 |

(51) Int. Cl.
*G01M 17/02* (2006.01)
*B60C 1/00* (2006.01)

(52) U.S. Cl. .................................... 73/146; 152/152.1
(58) Field of Classification Search .................. 73/146; 152/152.1

See application file for complete search history.

(56) References Cited

U.S. PATENT DOCUMENTS

| 2,152,883 | A | 4/1939 | Harrison | ................ 152/DIG. 3 |
| 3,364,965 | A | 1/1968 | Oubridge | ................. 152/209.5 |
| 3,645,313 | A | 2/1972 | Roberts et al. | ......... 152/209.17 |

(Continued)

FOREIGN PATENT DOCUMENTS

BR 200002924 10/2000

(Continued)

OTHER PUBLICATIONS

Abstracts for German 3939917, German 3937966, Europe 937615, Europe 989394, Japan 60-205037.

(Continued)

*Primary Examiner*—Andre J Allen
(74) *Attorney, Agent, or Firm*—Fitzpatrick, Cella, Harper & Scinto

(57) ABSTRACT

A tire includes, among the conventional tread pattern elements, at least one measuring element having a central zone and an encircling zone. In normal operation, the central zone 10 of a measuring element slides over the ground while, conversely, the tread as a whole does not slide over the ground. Measurements are carried out of the maximum adherence potential with the ground, at any moment, due to the central zone of a measuring element. In an alternative embodiment, the measuring element may comprise a circumferentially extending rib(s) or tread block(s) whose ground contact surface(s) is spaced at a lesser radial distance from the wheel axle than the spacing of the ground contact surfaces of the conventional tread blocks.

11 Claims, 14 Drawing Sheets

U.S. PATENT DOCUMENTS

| | | | |
|---|---|---|---|
| 4,319,620 A | 3/1982 | Knill | 152/209.5 |
| 4,480,671 A | 11/1984 | Giron | |
| 5,247,831 A | 9/1993 | Fioravanti | |
| 5,435,193 A * | 7/1995 | Halliday | 73/862.41 |
| 5,445,201 A | 8/1995 | Kukimoto et al. | 152/209.19 |
| 5,502,433 A | 3/1996 | Breuer et al. | |
| 5,821,434 A * | 10/1998 | Halliday | 73/862.541 |
| 5,864,056 A | 1/1999 | Bell et al. | |
| 5,913,240 A | 6/1999 | Drähne et al. | |
| 5,964,265 A | 10/1999 | Becherer | |
| 6,006,804 A | 12/1999 | Yokota | |
| 6,840,098 B2 * | 1/2005 | Halliday | 73/146 |
| 2004/0144167 A1 * | 7/2004 | Halliday | 73/146 |
| 2005/0065699 A1 * | 3/2005 | Bertrand | 701/80 |
| 2005/0155685 A1 | 7/2005 | Daval | 152/152.1 |
| 2005/0159874 A1 * | 7/2005 | Betrand | 701/80 |
| 2007/0016354 A1 * | 1/2007 | Engel et al. | 701/80 |
| 2007/0283744 A1 * | 12/2007 | Balkwill et al. | 73/9 |

FOREIGN PATENT DOCUMENTS

| | | |
|---|---|---|
| DE | 3937966 | 5/1991 |
| DE | 3939917 | 6/1991 |
| EP | 664230 | 7/1995 |
| EP | 0937615 | 8/1999 |
| EP | 0989394 | 3/2000 |
| EP | 1076235 | 2/2001 |
| JP | 0205037 | 10/1985 |
| JP | 61-263807 | 11/1986 |
| JP | 62-6802 | 1/1987 |
| JP | 6-171321 | 6/1994 |
| JP | 8-118918 | 5/1996 |
| WO | 9325400 | 12/1993 |

OTHER PUBLICATIONS

Abstract for Brazil 200002924.

Japanese Patent Abstract, Publication No. 60-205037, Hara Ikenosuke et al., Application No. 59-059474 [JP8459474], published Oct. 16, 1985.

Machine translations for German 3939917, German 3937966, Japan 6-171321.

* cited by examiner

MEASUREMENT OF ADHERENCE BETWEEN A VEHICLE WHEEL AND THE ROADWAY

CROSS REFERENCE TO RELATED APPLICATION

This application is a division of U.S. application Ser. No. 10/071,135, filed on Feb. 6, 2002, now U.S. Pat No. 7,267,148 which is a continuation-in-part of U.S. application Ser. No. 09/636,566, filed on Aug. 10, 2000 now abandoned. The disclosures of these prior applications are incorporated by reference herein in their entirety.

TECHNICAL FIELD OF THE INVENTION

The present invention relates to the adherence of a vehicle to a roadway. More particularly, it concerns the determination of adherence characteristics between a vehicle wheel equipped with a tire (a non pneumatic tire or a pneumatic tire) and the ground, based on obtaining physical parameters in the contact area between the wheel and the rolling surface.

BACKGROUND OF THE INVENTION

It has already been proposed to take permanent measurements in the tread of a tire while a vehicle equipped therewith is moving, in order to know in real time the stresses which develop between a tire and the ground. German Offenlegungsschrift DE 39 37 966 A1 may be consulted on this subject. Although of interest, such information is still insufficient, since the driver or even an automatic device, such as those covered by well known designations in the automotive field, e.g., "ABS" or "ESP", is still incapable of anticipating a deterioration in the adherence. One therefore makes do with noting a posteriori the exceeding of an adherence limit, and as rapid action as possible is taken to control the vehicle.

There exists in this respect a requirement to obtain indications "in real time" of the adherence conditions capable of affecting, in the moments which follow, the behavior of a vehicle, notably in cases where it undergoes a substantial acceleration, due to motive or braking forces or to a change in path. The present invention is aimed at supplying means and methods of providing such "real time" indications in an effective manner, by procuring as realistic information as possible on the safety margin which subsists in the driving of the vehicle.

As used herein, the following terms have the meanings set forth below:

"measuring element" means a part of the tread of the tire, e.g., a tread block or rib, whose structure is adapted to the aim pursued by the invention;

"adherence potential" means the ratio between the overall maximum tangential force which a measuring element, considered in its totality, may undergo during its contact with the ground at a given place, and the normal force applied to that element;

"friction potential" means the ratio between the local tangential stress and the local vertical stress which are exerted at a given point onto a rubber element sliding over the ground; and "available adherence margin" is the difference between the adherence potential of an element and the ratio between the overall tangential force and the overall vertical force actually applied to that element, considered in its totality, during its passage in the contact area.

SUMMARY OF THE INVENTION

In accordance with the invention, a tire is provided whose tread includes at least a first measuring tread element and at least one second tread element, each of the elements having a contact surface that, during normal operation of a vehicle equipped with the tire, comes into contact with the ground in a contact zone or area on each revolution of the tire, the first measuring element being configured such that, at least within a range of rolling conditions to be monitored, the contact surface thereof slides relative to the ground during its passage through the contact area. The tire further includes a sensor which is sensitive to at least a tangential force exerted in the contact surface of the first measuring element during its passage through the contact area.

The invention therefore proposes to adapt a part of the tread so that it exceeds the adherence limit in numerous rolling circumstances, even though the remaining part of the tread does not exceed the adherence limit, i.e., does not slip, and to make at least one appropriate measurement in that part. Knowledge of the adherence potential may thereby be obtained. The required sensor or sensors may be integrated into the tire tread, or may be external to the tire itself.

In one embodiment of a tire constructed in accordance with the invention, the first measuring element, viewed at the surface of the tread, has a central zone surrounded by an encircling zone. The central zone has a resistance to a force directed perpendicular to the surface of the tread which is less than that offered by the encircling zone. A sensor is disposed in order to achieve a measurement in the central zone, which sensor is sensitive to at least one tangential force exerted at the surface of the central zone.

The properties of the encircling zone are preferably identical to what is used in a significant part of the tread. The properties of the central measurement zone differ in that the central zone is rendered flexible compared with the encircling zone. Such flexibility of the central zone makes it possible to reduce the contact pressure on the ground, which permits the central zone to slide over the ground. There is meant by "properties" in this context an overall evaluation having a contribution stemming from the intrinsic characteristics of the material used, and in certain cases a contribution determined by the form given by the molding of the material, it even being possible for the latter to predominate. There is meant by "significant part" a part of the tread which is designed solely as a function of the wear properties which the designer of the tire desired to confer on the tire in question, in contrast to what is desired in order to perform a measurement.

In a second embodiment of a tire in accordance with the invention, the first measuring element has an area of contact with the ground which is positioned a distance from the wheel axle less than that of the second element, the elements being configured such that in normal operation their surfaces come into contact with the ground within the contact area, and also such that, at least within a range of rolling conditions to be monitored, the contact surface of the first element slides relative to the ground during its passage through the contact area. The tire also comprises means constituting a sensor within the first element, and the means that constitute such sensor are sensitive at least to a tangential force in the contact surface of the first element during the passage thereof through the contact area.

Preferably, the invention relates to a tire whose tread is made of rubber.

The invention also provides a method for detecting a characteristic of adherence between a wheel with a deformable tread and a surface along which the wheel is rolling, comprising the steps of:

(a) providing at least a first measuring element of the tread and at least one second element of the tread, each element having a contact surface with the ground, the contact surfaces being configured such that during normal operation the surfaces of the two elements come into contact with the ground and, at least within a range of rolling conditions to be monitored, the contact surface of the first element slides relative to the ground during its passage through the contact area;

(b) generating a first signal that represents a tangential force in the contact surface of the first element, (c) detecting a variation of the first signal that characterizes a loss of adherence;

(d) generating an estimate of the friction potential in the contact surface of the first element; and (e) producing an estimate of the adherence potential of the tire.

In one embodiment of the method of the invention, the steps comprise:

(a) providing in the tread at least a first measuring element whose surface is intended to come into contact with the ground on each revolution of the tire, the measuring element, viewed at the surface of the tread, having a central zone surrounded by an encircling zone, the central zone being arranged to slide over the ground with a level of stress parallel to the surface of the ground which is substantially weaker than the level of stress parallel to the surface of the ground beyond which the encircling zone will slide over the ground;

(b) arranging a sensor in order to achieve a measurement in the central zone, the sensor being sensitive to at least one parameter reflecting a tangential force exerted at the surface of the central zone;

(c) generating a first signal representative of a tangential force in the contact surface of the central zone;

(d) detecting a variation in the first signal which is characteristic of a loss of adherence;

(e) producing an estimate of the friction potential in the contact surface of the central zone; and (f) producing an estimate of the adherence potential of the tread.

According to a second embodiment, the method comprises the steps of:

(a) providing at least a first measuring element of the tread having an area of contact with the ground located at a distance from the wheel axle less than the distance of the ground contact area of at least one second tread element, the separation between these contact areas being such that during normal operation the surfaces of the two elements both come into contact with the ground and, at least within a range of rolling conditions to be monitored, the contact surface of the first element slides relative to the ground during its passage in the contact area;

(b) generating a first signal that represents a tangential force in the contact surface of the element nearest to the axle;

(c) detecting a variation of the first signal that characterizes a loss of adherence;

(d) producing an estimate of the friction potential in the contact surface of the first element; and (e) producing an estimate of the tire's adherence potential.

The invention also makes it possible to estimate the available adherence margin by the determining difference between the adherence potential of the tire and the ratio between the tangential force and the vertical force which are actually applied to the tire. Thus, the additional step of measuring or estimating the vertical force applied to the contact surface of the first element is required. As a non-limiting illustration, it is possible to estimate the tangential force, for example in the longitudinal direction, as well as the vertical force by the means described in the U.S. Pat. No. 5,913,240. It is also possible to estimate the tangential force and the vertical force by measures all of which are conducted in the tread. Other details are given on this subject below.

According to a further embodiment, the invention provides an estimate of the available adherence margin without having recourse to measurement or estimation of the vertical and tangential forces effectively applied to the tire. For this, the invention proposes a method for detecting an adherence characteristic between a wheel with a deformable tread and the ground along which it is rolling, which comprises the steps of:

(a) providing in the tread at least a first measuring element and at least one second element, each element having a contact surface with the ground, the contact surfaces being configured such that during normal operation the surfaces of the two elements come into contact with the ground and, at least within a range of rolling conditions to be monitored, the contact surface of the first element slides relative to the ground during its passage through the contact area;

(b) generating a first signal that represents a tangential force in a zone of the contact surface of the first element;

(c) detecting by virtue of the first signal the instant when the first element enters the contact area;

(d) detecting the instant when the first signal undergoes a change that characterizes a loss of adherence; and (e) producing an indication characterizing an available adherence margin from a function of the first signal between the instant when its entry into the contact area is detected and the instant when the characteristic change is detected.

Either of the two tire embodiments described above may be used in the practice of this method for determining the available adherence margin. In such case, step a) of the method would parallel step a) of the foregoing methods for determining the adherence potential.

DESCRIPTION OF EXEMPLARY EMBODIMENTS

Figure 1:
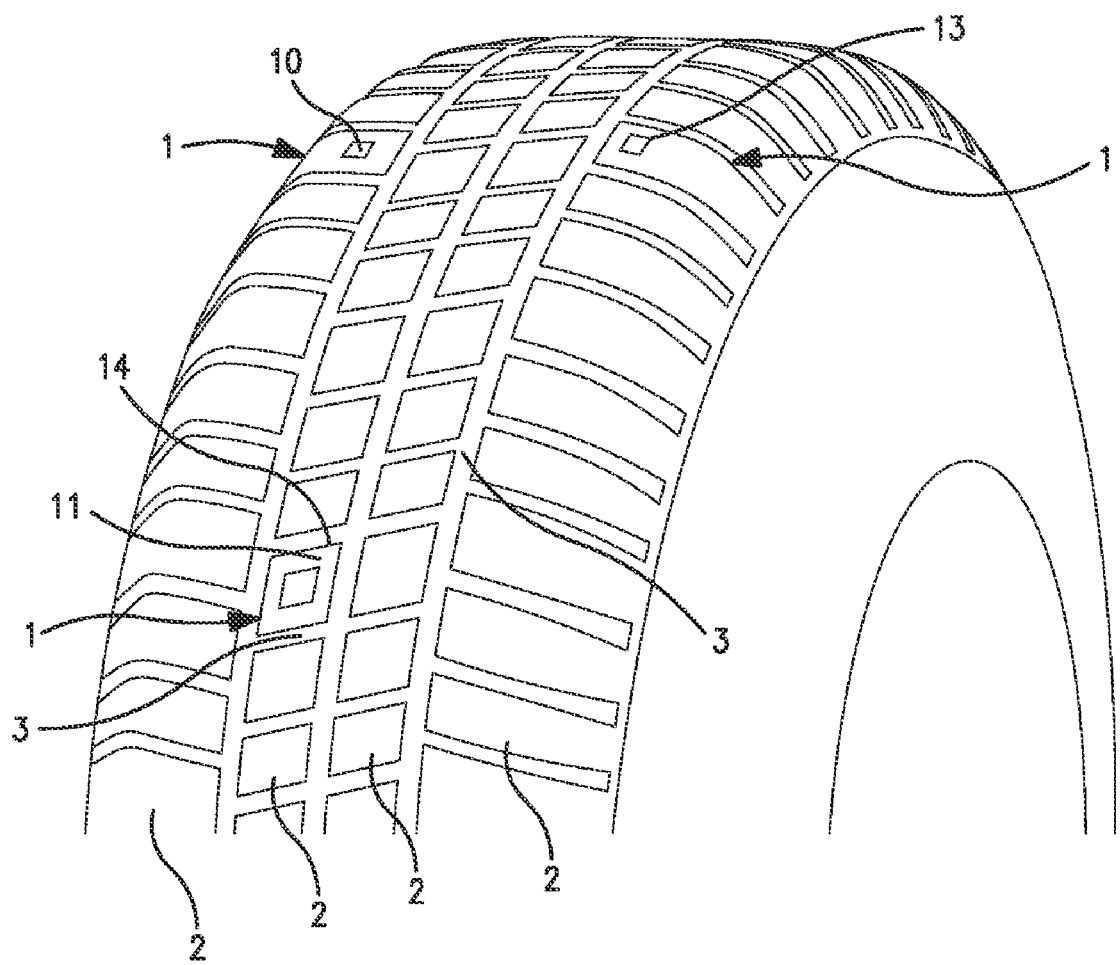
FIG. 1 is a partial overall view of a tread of a tire, showing a first embodiment of a measuring element of the tread adapted to the measurement in its environment.

There is seen in FIG. 1 a tire exhibiting a pattern on its tread. The pattern is chosen solely as an example and is not limiting. The pattern comprises a certain number of rubber tread blocks 2, of sensible and variable shape, according to the rules of the art of designing treads. Herein, a block of rubber limited over its entire periphery by fairly deep recesses 3 is called a rubber "tread block". In accordance with one embodiment of the invention, a certain number of such tread blocks are adapted as described below in order to make measuring elements 1 of them.

Each measuring element 1 (see also FIGS. 2 and 3) includes a central zone 10 surrounded by an encircling zone 11. A sensor 12 is arranged in the interior of the central zone (see FIG. 3). Such a sensor is disposed preferably radially inwardly of the part of the thickness of the tread intended to become worn ("radially" is used according to the conventional meaning in the tire field), and preferably is of a type able to measure stresses or displacements. It is a matter of measuring a state or states related to the deformations or stresses which the tire undergoes during the rolling, at the contact surface opposite such place, in the longitudinal and transverse directions. Use is made, for example, of a Hall effect device, comprising a magnetic element 120 and at least one device with Hall effect 121. The configuration and operation of suitable sensors is described in more detail hereinafter.

Figure 2:
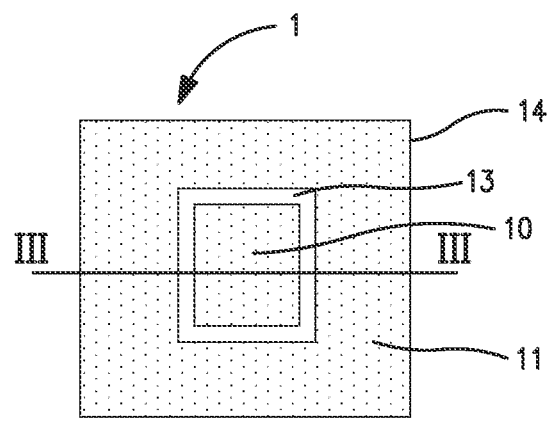
FIG. 2 is an enlargement enabling the first embodiment of the measuring element shown in FIG. 1 to be better viewed.
Figure 3:
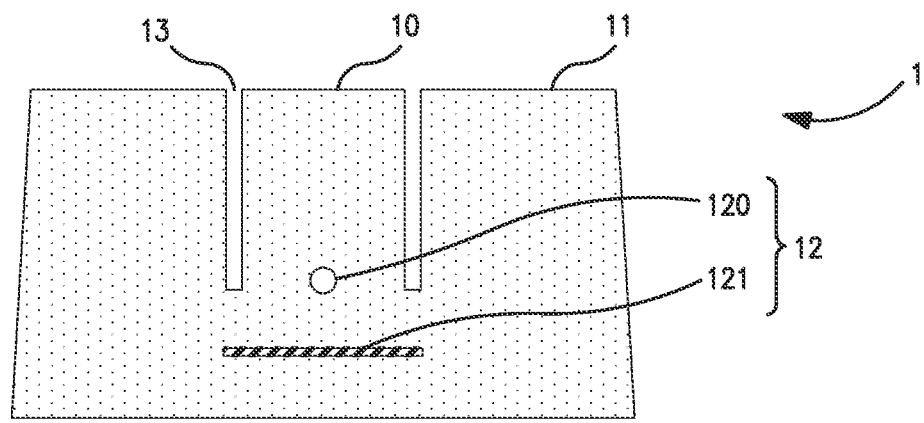
FIG. 3 is a radial cross-section along the line III-III in FIG. 2.

In FIGS. 1 to 3 is seen a thin recess strip 13, that is to say a cutout of small width compared with the width of the recesses 3 adjacent to the tread blocks 2. In a wide range of stresses developed on the contact of the tire with the ground during normal running, a large part, if not the whole, of the central zone 10 of the measuring element 1 slides over the ground. It has been found that this occurs even with free rolling (no torque) at low speed, including on ground surfaces having strong adherence with the tire. This phenomenon of sliding of the central zone occurs at least during a part of each passage of the measuring element in the contact area with the ground. The guarantee that the phenomenon of sliding of the measuring element 1 will occur makes it possible to measure the friction potential with the ground. In the remainder of the tread, on the other hand, only small parts slide over the ground, and these possibly sliding parts are far too small to provide an exploitable measurement for arriving at the friction potential.

It has been noticed that there exists in the center of a tread block, that is to say at a certain distance from the edges 14, an excellent correlation between the forces directed tangentially, i.e., those forces providing all the accelerations of the vehicle, including guiding it, and occurring at the contact surface, and the parallel forces which are able to be measured more in the interior, beyond the limit of the wear part of the tread.

According to a first embodiment, the thin recess strip 13 relieves of stress the material situated radially beneath the surface of the central zone 10 compared with the adjacent material situated beneath the encircling zone 11. Preferably, the thickness of the thin strip 13 is approximately 0.3 mm to 2 mm. In some cases, the thin strip may be at least partially inclined relative to the central plane of the tire.

The invention thus relates per se to a tire whose tread comprises at least one measuring element 1 whose surface is intended to come into contact with the ground on each revolution of the tire, the measuring element 1, viewed at the surface of the tread, having a central zone 10 surrounded by an encircling zone 11, a thin recess strip 13 relieving of stress the material situated radially beneath the surface of the central zone 10 as compared with the adjacent material situated beneath the encircling zone 11, a sensor 12 being arranged in order to achieve a measurement in the central zone 10, such sensor 12 being sensitive to at least one tangential force exerted at the surface of the central zone.

The relief of stress provided by the thin recess strip 13 makes it possible to carry out the measurement envisaged in a very acceptable manner. It is thought that this is because the central zone 10 offers less resistance to a force directed perpendicular to the surface of the tread than the resistance offered by the encircling zone to a force directed perpendicular to the surface of the tread. This makes it possible to prevent the occurrence of ground contact pressures which are too high to permit sliding of the central zone. The same observation is applicable to the other embodiments and variants described below with reference to FIGS. 4-14. Hence, the general description of the invention given above.

An advantage of the invention is to be able in this way to comprehend the available adherence margin up to total wear of the tire, by means of a measurement of the friction potential made as indicated.

What is set out here is all the more usable for a tread devoid of pattern.

The tire adapted in this way makes it possible to estimate the adherence potential, a concept defined above and used with reference to the tread as a whole, and the friction potential, a concept also defined above and used with reference to an individual measuring element.

Figure 10:
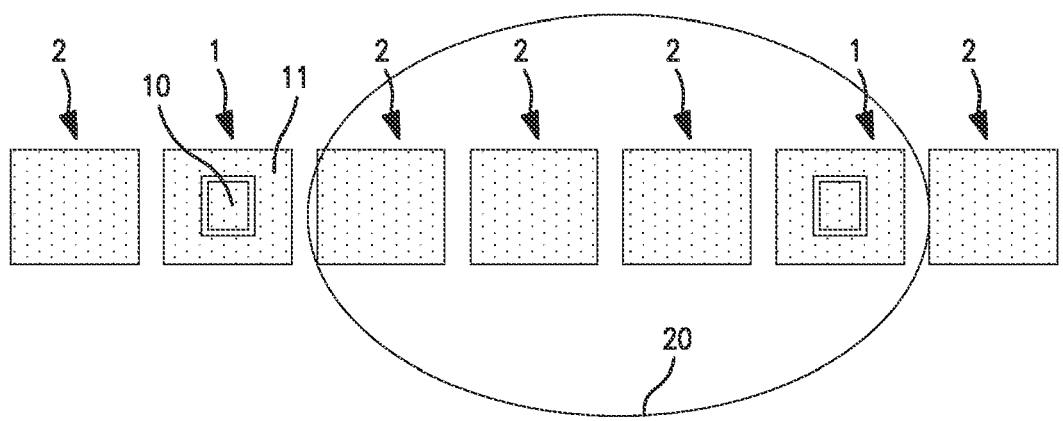
FIG. 10 illustrates a plurality of measuring elements spaced about the circumference of a tire.

With one or more appropriate sensors 12, sensibly arranged, it is possible to obtain the measurements during the whole service life of the tire. It is naturally desirable that the part of the tread of the tire specific to the measurement be as small as possible, or more fundamentally that such part does not detract from the performance of the tire. It may be beneficial, therefore, to limit it to one or a small number of rubber tread blocks. The desired information may be obtained by making a single measurement per revolution of the tire. In an advantageous manner, as shown in FIG. 10, the tire may comprise sufficient measuring elements 1 to ensure that there is always at least one of them in the contact zone or area 20 of the tire with the ground. It is not strictly necessary that all of the tires on a vehicle be covered by such measurements. One tire per side may be sufficient, although more than one tire may be used if desired.

Figure 4:
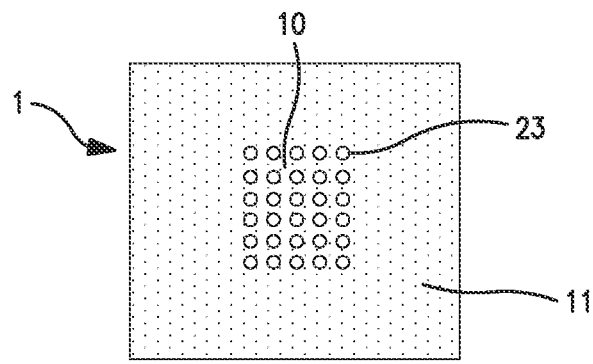
FIG. 4 illustrates a second embodiment of a measuring element.

Other embodiments of the invention may be envisaged. For example, it is possible to mold in the central zone 10 a plurality of cutouts in the form of wells. In certain cases, the cutouts in the form of wells may be at least partially inclined. This is illustrated in FIG. 4. The presence of the cutouts 23 makes it possible to carry out the measurements envisaged in a very acceptable manner.

Thus, the invention also relates per se to a tire whose tread comprises at least one measuring element 1 whose surface is intended to come into contact with the ground on each revolution of the tire, the measuring element, viewed at the surface of the tread, having a central zone 10 surrounded by an encircling zone 11, a plurality of cutouts 23 being molded into the central zone, a sensor 12 being disposed in order to achieve a measurement in the central zone 10, such sensor 12 being sensitive to at least one tangential force exerted at the surface of the central zone 10.

Figure 5:
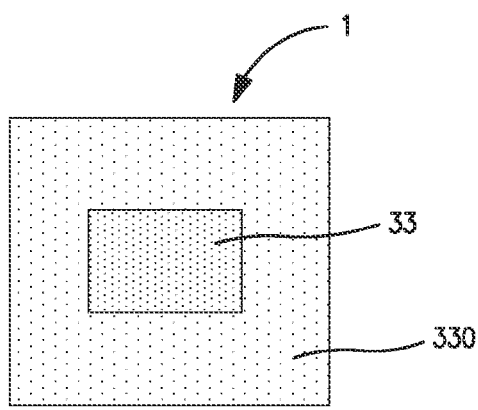
FIG. 5 illustrates a third embodiment of a measuring element.

In a third embodiment, the Young's modulus of the material situated beneath the central zone 10 is less than the Young's modulus of the adjacent material situated beneath the encircling zone 11. This is illustrated in FIG. 5. The use of different materials makes it possible to carry out the measurement envisaged in a very acceptable manner.

Thus, the invention also relates per se to a tire whose tread comprises at least one measuring element 1 whose surface is intended to come into contact with the ground on each revolution of the tire, the measuring element, viewed at the surface of the tread, having a central zone 33 surrounded by an encircling zone 330, the Young's modulus of the material situated beneath the central zone 33 being smaller than the Young's modulus of the adjacent material situated beneath the encircling zone 330, a sensor 12 being arranged in order to achieve a measurement in the central zone 33, such sensor being sensitive to at least one tangential force exerted at the surface of the central zone 33.

The variants set out above may be advantageously combined. It is thus possible to maintain, during the whole service life of the tire, a vertical contact pressure between the central zone of a measuring element and the ground which is sufficient to guarantee good accuracy in the measurement of the adherence potentials. It is therefore possible to combine two or more concepts set out above; the relief of stress by a thin recess strip closed on itself being a first concept, the molding of a plurality of cutouts being a second concept, and the use of materials having a different Young's modulus being a third concept.

Figure 6:
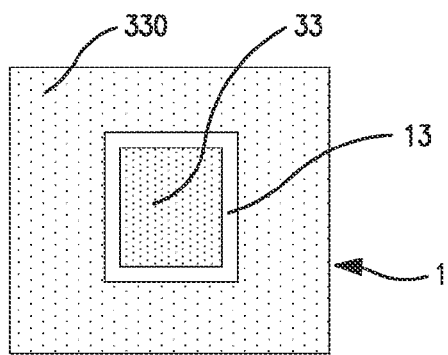
FIG. 6 illustrates a combination of the first and third embodiments of a measuring element.

FIG. 6 illustrates an embodiment combining the first and third concepts of a measuring element. It is noted that it is possible to envisage that the central zone 33 of the measuring element is in this case constructed of a material with a Young's modulus greater than the Young's modulus of the material of which the encircling zone 330 is constructed. The materials of the latter may be adjusted in one direction or the other in order to promote to a greater or lesser extent the resistance to wear and the tendency to slide.

Figure 7:
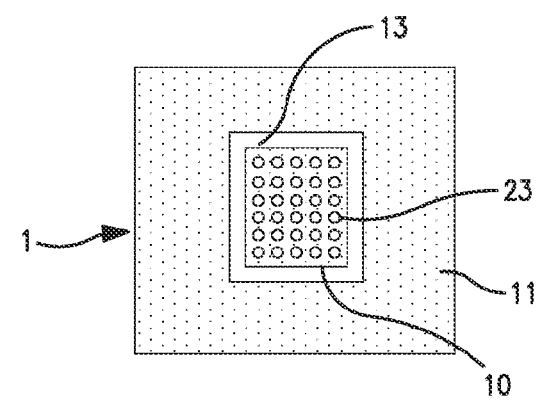
FIG. 7 illustrates a combination of the first and second embodiments of a measuring element.

FIG. 7 illustrates an embodiment combining the first and second concepts of a measuring element. It would naturally be possible to combine in a single measuring element 1 the characteristics of the three concepts presented.

Figure 8:
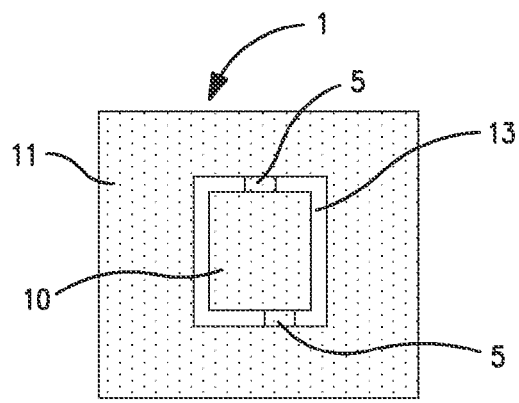
FIG. 8 illustrates a first variant of the first embodiment of a measuring element.
Figure 9:
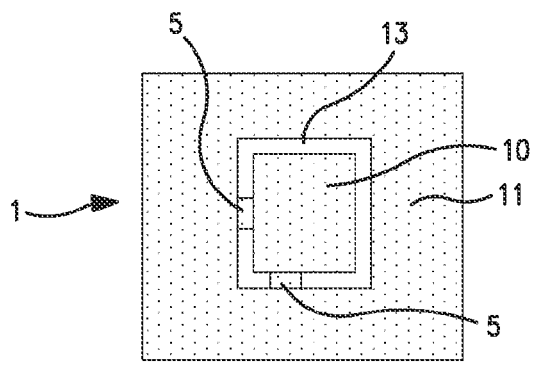
FIG. 9 illustrates a second variant of the first embodiment of a measuring element.

FIGS. 8 and 9 illustrate two variants of the first embodiment of a measuring element 1, in which rubber bridges 5 connect locally the rubber beneath the central zone 10 to the rubber beneath the encircling zone 11.

With respect to all of the foregoing embodiments, it is generally advantageous that the surface area of the central zone be at least substantially equivalent to the surface area of the encircling zone.

Figure 11:
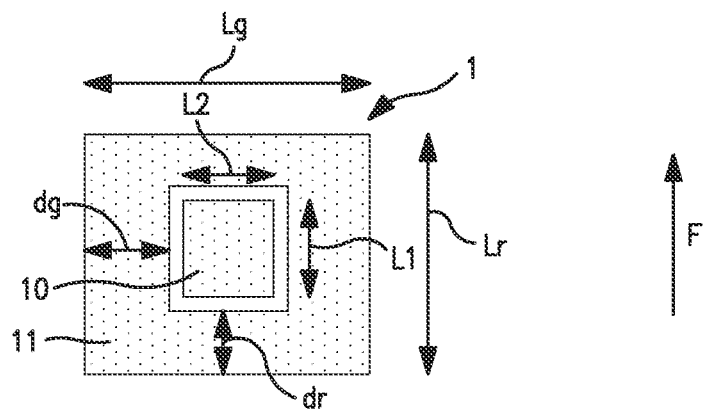
FIG. 11 illustrates preferred dimensional relationships for the measuring element.

In accordance with the invention, the components of each measuring element 1 preferably have the following dimensional relationships, as illustrated in FIG. 11:

$L_r$ being the length of the measuring element 1 in the preferred rolling direction shown by the arrow F, $L_g$ being the length of the measuring element in the direction perpendicular to the preferred rolling direction, $L_1$ being the length of the central zone 10 in the preferred rolling direction, $L_2$ being the length of the central zone 10 in the direction perpendicular to the preferred rolling direction, $d_r$ being the minimum length measurable on the encircling zone 11 in the preferred rolling direction, $d_g$ being the minimum length measurable on the encircling zone 11 in the direction perpendicular to the preferred rolling direction, the following relations are obeyed: $dr>Lr/10$, $dg>Lg/10$, $Lr/5<L1<4Lr/5$ and $Lg/5<L2<4Lg/5$.

Figures 12, 13, 14:
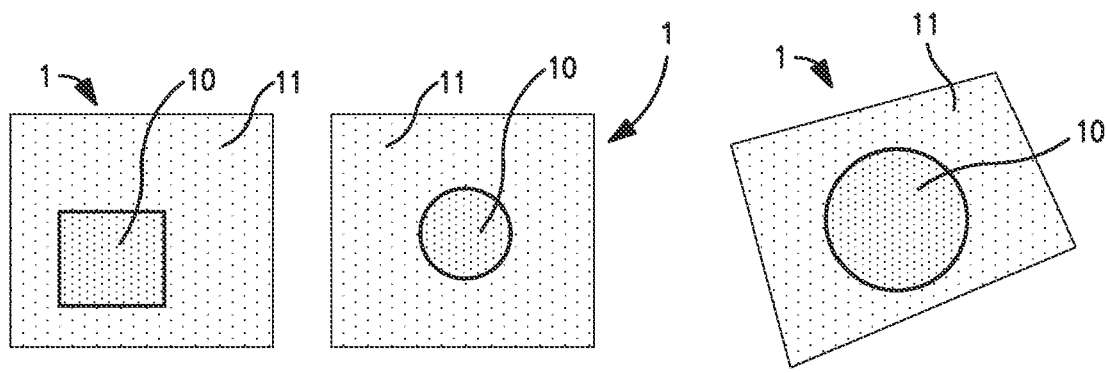
FIG. 12 illustrates an embodiment variant applicable to all the embodiments presented above.
FIG. 13 illustrates another embodiment variant applicable to all the embodiments presented above.
FIG. 14 illustrates another possibility of an embodiment variant applicable to all the embodiments presented above.

FIGS. 12 to 14 show examples of the numerous variants of shape (which are in fact infinite) which can be given to the central zone 10 and to the encircling zone 11. Preferably, however, the following rule will be obeyed: the center of mass of the measuring element 1 is in the central zone 10.

Figure 15:
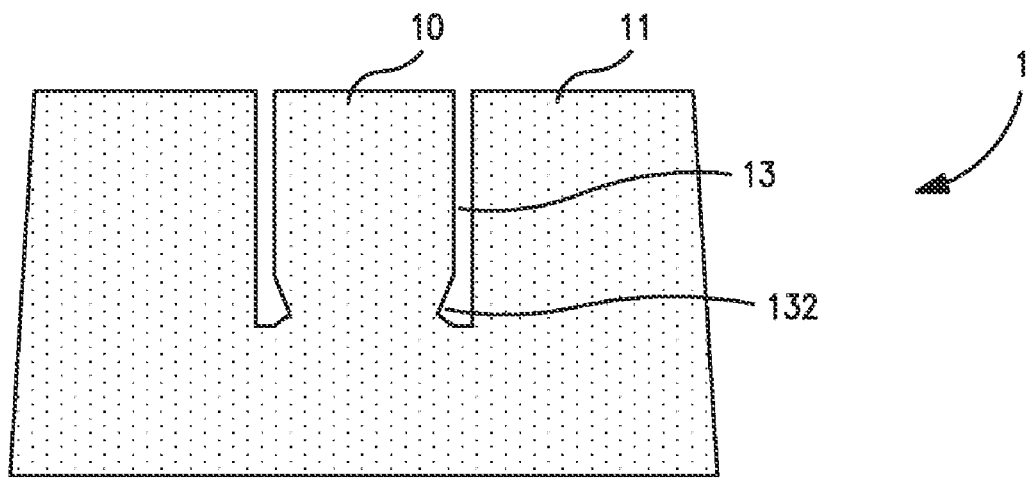
FIG. 15 illustrates a possible variation, applicable to the embodiments including the first embodiment.
Figure 16:
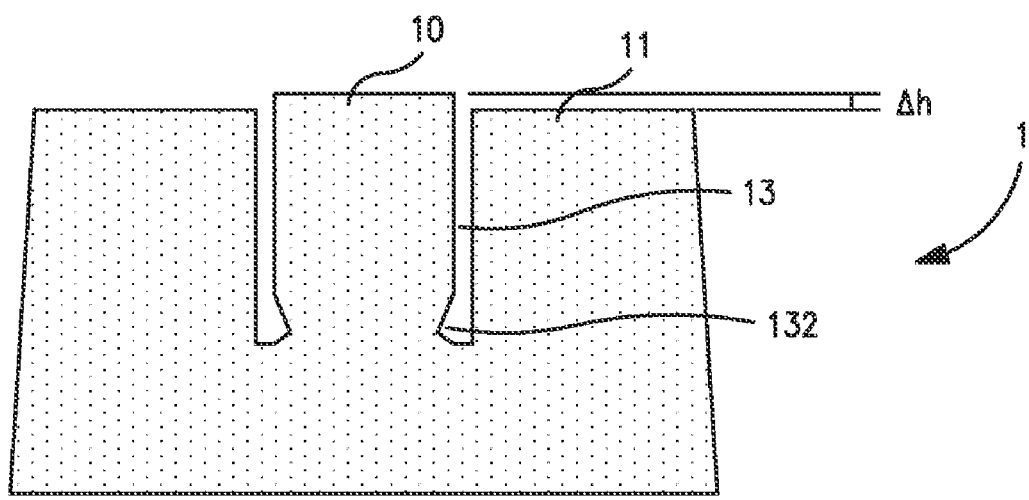
FIG. 16 illustrates another variation applicable to the embodiments including the first embodiment.
Figure 17:
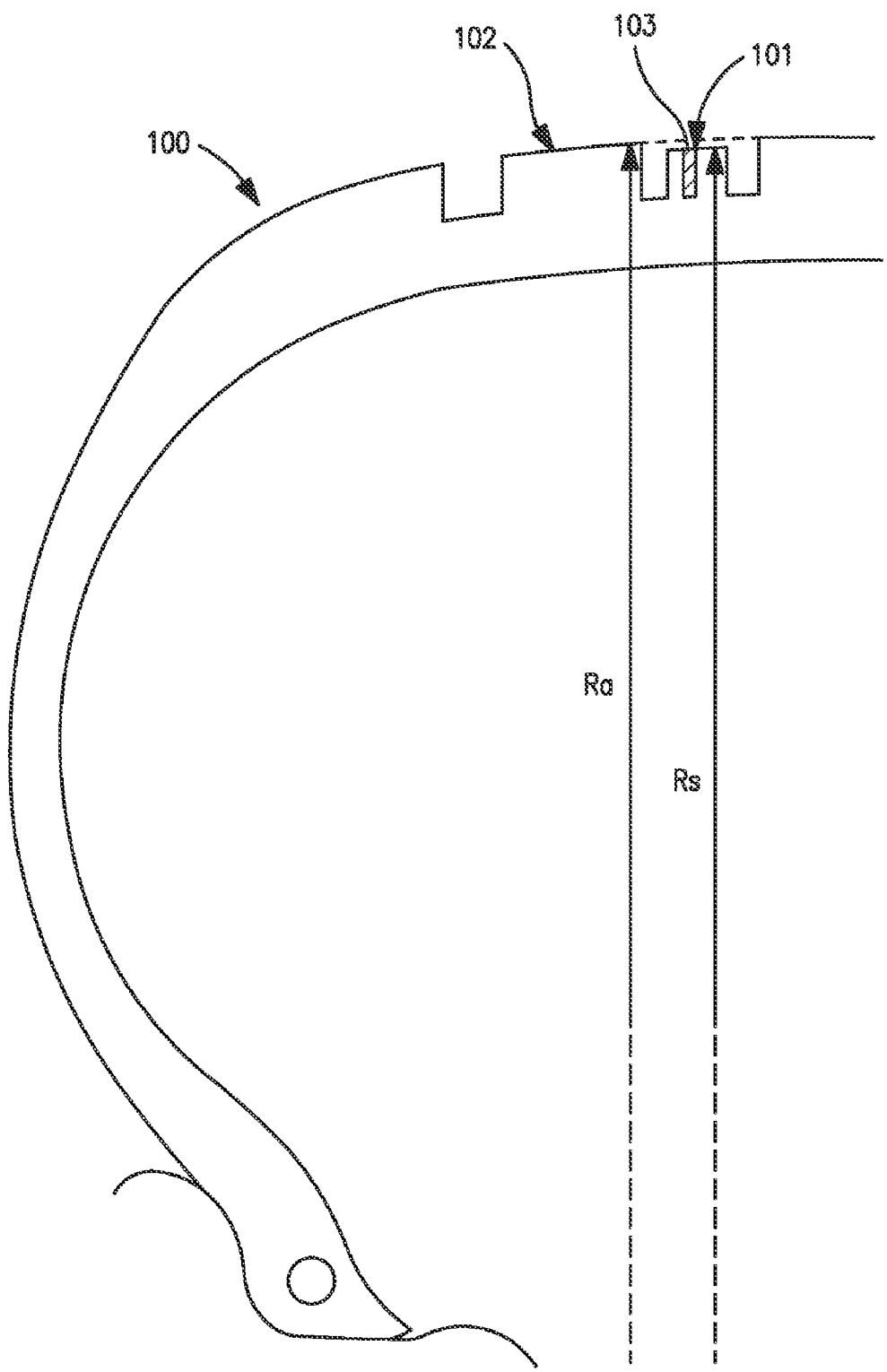
FIG. 17 is a radial section of a tire constructed in accordance with another embodiment of the invention.

In the embodiments shown in FIGS. 15 and 16, beneath the thin recess strip 13 is a cavity 132 of a larger width than the width of the strip 13. This variation favors the reliability of the measurements taught by this invention at high wear states of the tread. In the variation shown in FIG. 16, the central zone 10 features a difference in radial height h. The difference in radial height h could be positive, as shown, or negative. This offers a parameter of design to adjust the contact pressure on the ground of the central zone 10. On an experimental basis and depending on the exact shape of the central zone 10 (shape in a view similar of that of FIGS. 11-14), it could be desirable to provide such a difference of radial height of the central zone 10 with respect to the encircling zone 11 in order to achieve almost identical wearing rate of the central zone 10 and the encircling zone 11.

According to another aspect of the invention, methods are provided for detecting one or more adherence characteristics of the tread with the ground.

Based on a pre-established relation for linking the friction potential and the adherence potential of the tire, on the one hand, and a procedure for regular recalibration using, for example, the property according to which the maximum adherence potential of the tire under all roadway conditions combined evolves or changes only slightly, it is possible to deduce the value of the adherence potential of the tire from the value of the shear stress, or of any signal representative of the shear stress, exerted on the central zone of a measuring element. In accordance with the invention, this may be done by generating a first signal which represents a tangential force in the contact surface of a measuring element, detecting a variation in such signal which characterizes a loss of adherence between the contact surface and the road, producing therefrom an estimate of the friction potential in the contact surface of the measuring element, and then producing an estimate of the adherence potential of the tire. The recalibration procedure is necessary because the pressure beneath the central zone of a measuring element may evolve or change during the use of the tire, for example, as a function of the wear on the tire, for identical conditions of load on the tire and of inflation pressure, and such evolution or change of the pressure introduces a variable which modifies the relation between the shear stress exerted on the central zone of a measuring element and the adherence potential of the tire.

If a measuring element is equipped to measure the vertical stress at the same point, it is possible to calculate the coefficient of friction between the measuring element and the ground by calculating the ratio between the shear stress and the vertical stress. In this case, it is perhaps not necessary to perform a regular recalibration in order to evaluate the adherence potential of the tire.

Consequently, in an advantageous embodiment of the proposed method of detection, the steps aimed at detecting a variation in a first signal representative of the shear stress and at producing an estimate of the adherence potential in the contact surface of the tire comprise the following:

(a) generating a second signal representative of a vertical force in the contact surface of the central zone;

(b) generating from the first and second signals a third signal representative of the ratio between the tangential force and the vertical force;

(c) detecting a variation of the third signal characteristic of a loss of adherence;

(d) producing an estimate of the friction potential in the contact surface of the central zone; and (e) based on the friction potential, producing an estimate of the adherence potential of the tread.

According to another aspect of the invention, it is proposed to estimate the available adherence margin without carrying out a measurement or an estimate of the vertical force actually applied to the tire. For this, the invention proposes a method for detecting a characteristic of adherence between a wheel possessing a deformable tread and the ground surface, comprising the following steps:

(a) providing in the tread at least one measuring element whose surface is intended to come into contact with the ground on each revolution of the tire, the measuring element, viewed at the surface of the tread, having a central zone surrounded by an encircling zone, the central zone being arranged to slide over the ground at a level of stress parallel with the surface of the ground which is substantially weaker than the level of stress parallel with the surface of the ground beyond which the encircling zone will slide over the ground;

(b) disposing a sensor in order to achieve a measurement in the central zone, the sensor being sensitive to at least one parameter reflecting a tangential force exerted at the surface of the central zone;

(c) generating a first signal representative of a tangential force in the central zone;

(d) detecting from the first signal the instant of entry into the contact area of the central zone;

(e) detecting from the first signal the instant at which the first signal undergoes a variation characteristic of a loss of adherence; and (f) producing an indication characteristic of an available adherence margin based on a function of the first signal between the instant of detection of entry into the contact area and the instant of detection of the characteristic variation.

The function of the first signal in step f) is advantageously the ratio between the mean value of the first derivative of the first signal plotted over time and the value of the first signal at the point characteristic of a loss of adherence. As a variant, the function of the first signal may be the time interval separating the detections of steps d) and e).

It is also possible to envisage carrying out measurements in the part of the tread external to a measuring element 1, that is to say, in the part of the tread whose properties owe nothing to the concern to carry out measurements. In such case, the method proposed by the invention comprises in addition the following steps:

(a) disposing a sensor to achieve a measurement in a zone of the contact surface of the tread which is external to the measuring element or elements, the sensor being sensitive to at least one parameter reflecting a tangential force exerted at the surface of the external zone;

(b) producing a first functional tread signal representative of a tangential force in a zone of the contact surface of the tread which is external to the measuring element or elements;

(c) producing a second functional tread signal representative of a vertical force in a zone of the contact surface of the tread which is external to the measuring element or elements;

(d) producing an indication characteristic of the tangential force applied to the tire, based on the integration of the first functional tread signal between the instants of the start and the end of contact with the ground of the external zone and over the whole width of the tire;

(e) producing an indication characteristic of the vertical force applied to the tire, based on the integration of the second functional tread signal between the instants of the start and the end of contact with the ground of the external zone and over the whole width of the tire; and (f) determining the available adherence margin by the difference between the adherence potential of the tread and the ratio between the tangential force and the vertical force applied to the tread.

As still a further embodiment, the invention proposes a method of detecting a characteristic of adherence between a wheel possessing a deformable tread and the ground surface, comprising the following steps:

(a) providing in the tread at least one measuring element whose surface is intended to come into contact with the ground on each revolution of the tire, the measuring element, viewed at the surface of the tread, having a central zone surrounded by an encircling zone, the central zone being arranged to slide over the ground at a level of stress parallel with the surface of the ground which is substantially weaker than the level of stress parallel with the surface of the ground beyond which the encircling zone will slide over the ground;

(b) disposing a sensor in order to achieve a measurement in the central zone, the sensor being sensitive to at least one parameter reflecting a tangential force exerted at the surface of the central zone;

(c) disposing a sensor in order to achieve a measurement in a zone of the contact surface of the tread which is external to the measuring element or elements, the sensor being sensitive to at least one parameter reflecting a tangential force exerted at the surface of the external zone;

(d) generating a first signal representative of a tangential force in the central zone;

(e) generating a second signal representative of a tangential force in the external zone; and (f) producing an indication characteristic of an available adherence margin based on a comparison of said first and second signals.

Still other embodiments of a method for determining an adherence or grip characteristic between a wheel with a deformable tread and a surface along which it is rolling, and of a tire useful in making such determinations, are disclosed in FIGS. 17-23.

As there disclosed, a tire 100 according to the invention includes one or more circumferentially extending ribs or tread blocks 101, whose outer surface has a radius Rs smaller than the radius Ra of the surface of the adjacent ordinary ribs or tread blocks 102 of the tire. The rib or tread block 101 is encompassed by the definition of "measuring element" as set out above. It is also referred to herein as a "sacrificed rib" or "sacrificed tread block". U.S. Pat. No. 4,480,671, the disclosure of which is hereby incorporated by reference for all purposes, shows such a sacrificed rib (see lateral rib 8). In contrast, the other portions of the tire pattern are referred to as an "ordinary ribs" or "ordinary tread blocks", or, more generally, as "second elements". Those skilled in the art know that the difference between Ra and Rs can automatically be maintained during the wear of the tire in normal service. An advantage of the invention is that the available adherence margin can therefore be determined until the tire is completely worn down, by virtue of a measurement of the friction potential carried out on a sacrificed rib.

During normal operation the sacrificed rib 101 slides over the ground while the ordinary rib 102 does not slide over the ground. A measurement of the maximum adherence potential on the ground is made by virtue of the sacrificed rib 101.

Inside each sacrificed rib or sacrificed tread block 101, one or more sensors 103 enable the measurement of the deformations or stresses to which the rib or tread block is subjected while the tire is rolling, these being measured in the longitudinal and transverse directions. The stresses or deformations can also be measured in the vertical direction, and this improves the performance of the system.

With an appropriate sensor 103 these measurements can be obtained throughout the life of the tire. It is of course desirable that the part of the tire tread specifically involved in the measurement should be as small as possible, or more fundamentally, that it should not adversely affect the tire's performance. For that reason, it may be advantageous to limit the part in question to one or a small number of rubber tread blocks, or to limit it to a circumferential rib as narrow as possible. The information desired can be obtained by making a single measurement for each rotation of the tire. As with the earlier embodiments, the measurements need only be made on one tire on each side of the vehicle, although more than one tire on each side may be utilized if desired.

Figure 18:
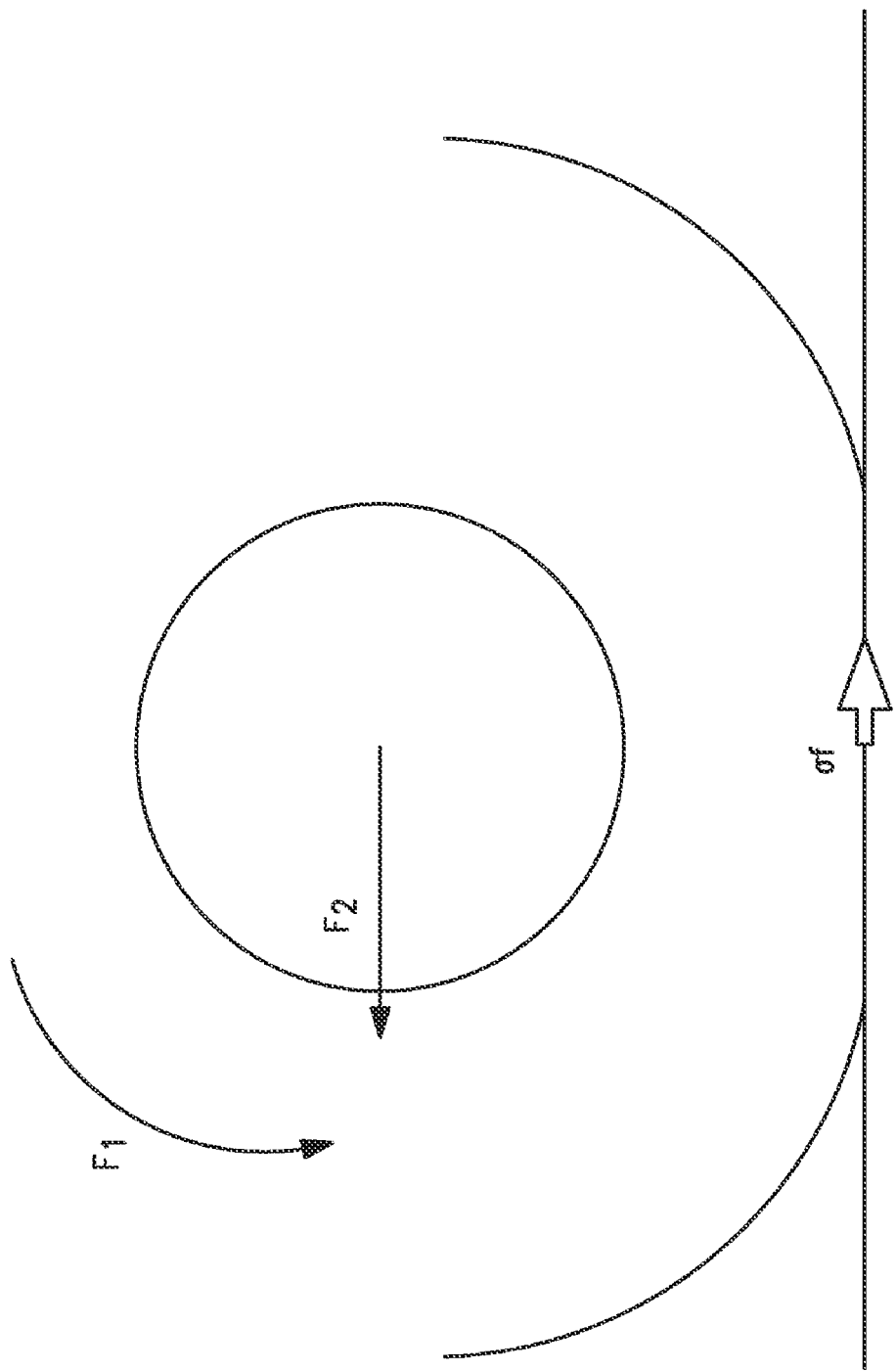
FIG. 18 is a schematic representation of the operation of a tire.

As illustrated in FIG. 18, during free rolling (i.e. with no coupling to an engine and no braking) and with F1 representing the rotation direction and F2 the direction of movement and when the tire is rolling in a straight line along a road, when a point at the surface of a sacrificed rib 101 comes into contact with the road, a braking sheer stress develops at the interface between the sacrificed rib 1001 and the road. This is added to the sinusoidal stress normally acting on all the tire ribs, an example of which is represented by the curve 105 relating to the rib 102 in FIG. 19. The resultant stress on the sacrificed rib 101 takes the form of the curve 106 relating to the rib 101 in FIG. 19. This stress increases from the instant when contact begins until the instant when the shear stress reaches the maximum value permitted by the friction potential of the rubber against the ground.

Figure 19:
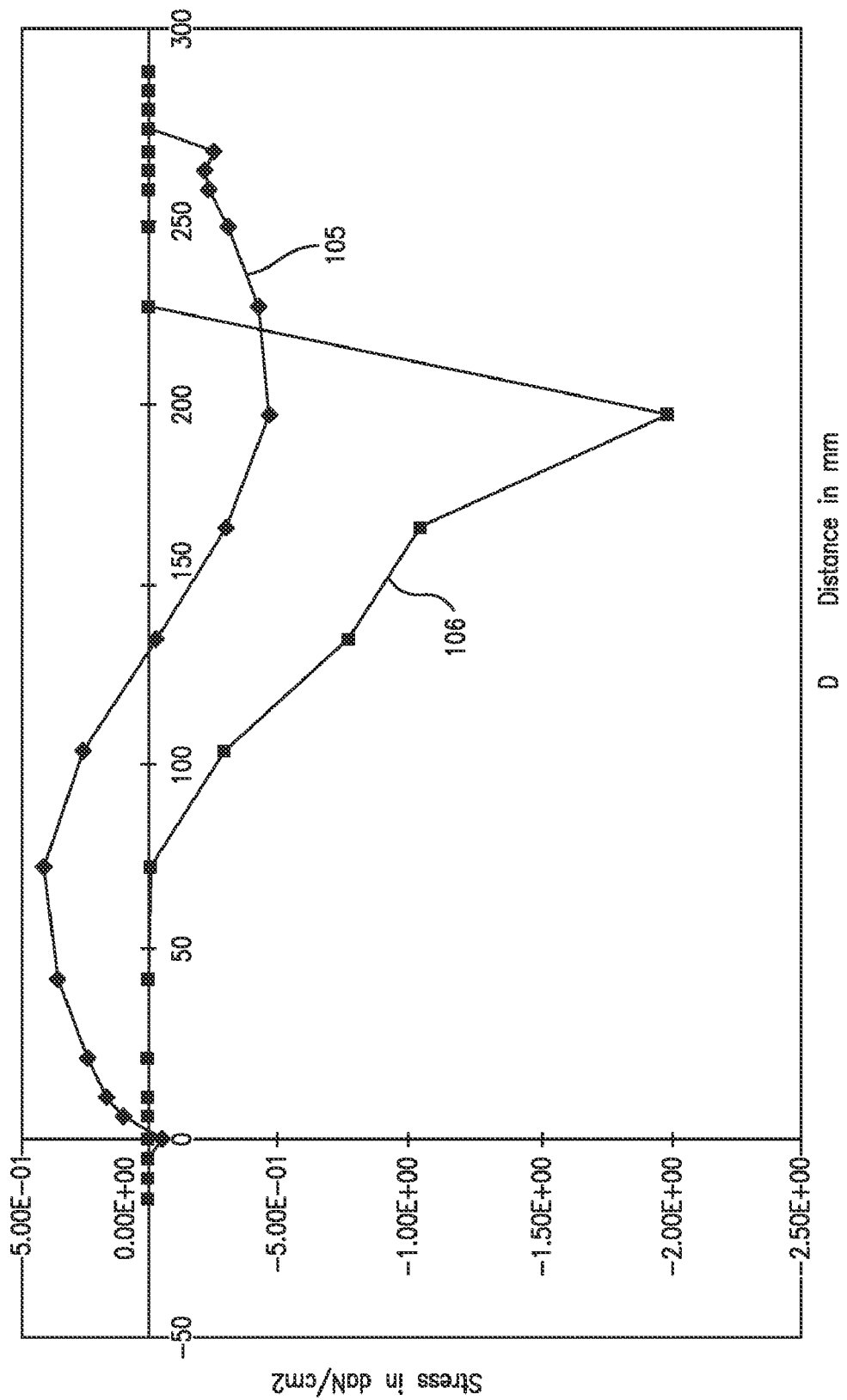
FIG. 19 is a graphical representation of the observations typical for the invention in an idealized case.

FIG. 19 presents the theoretical case of a friction potential which is infinite or very large. It shows the longitudinal shear stresses (in daN/cm$^2$) in a sacrificed rib 101 and the stresses in a normal rib 102 adjacent to the sacrificed rib 101, in the area of contact, as a function of the distance D (in mm) between the edge of the contact area and the point considered. In this case, the absolute value of the shear stress increases until the instant when contact between such point and the road ceases.

Figure 20:
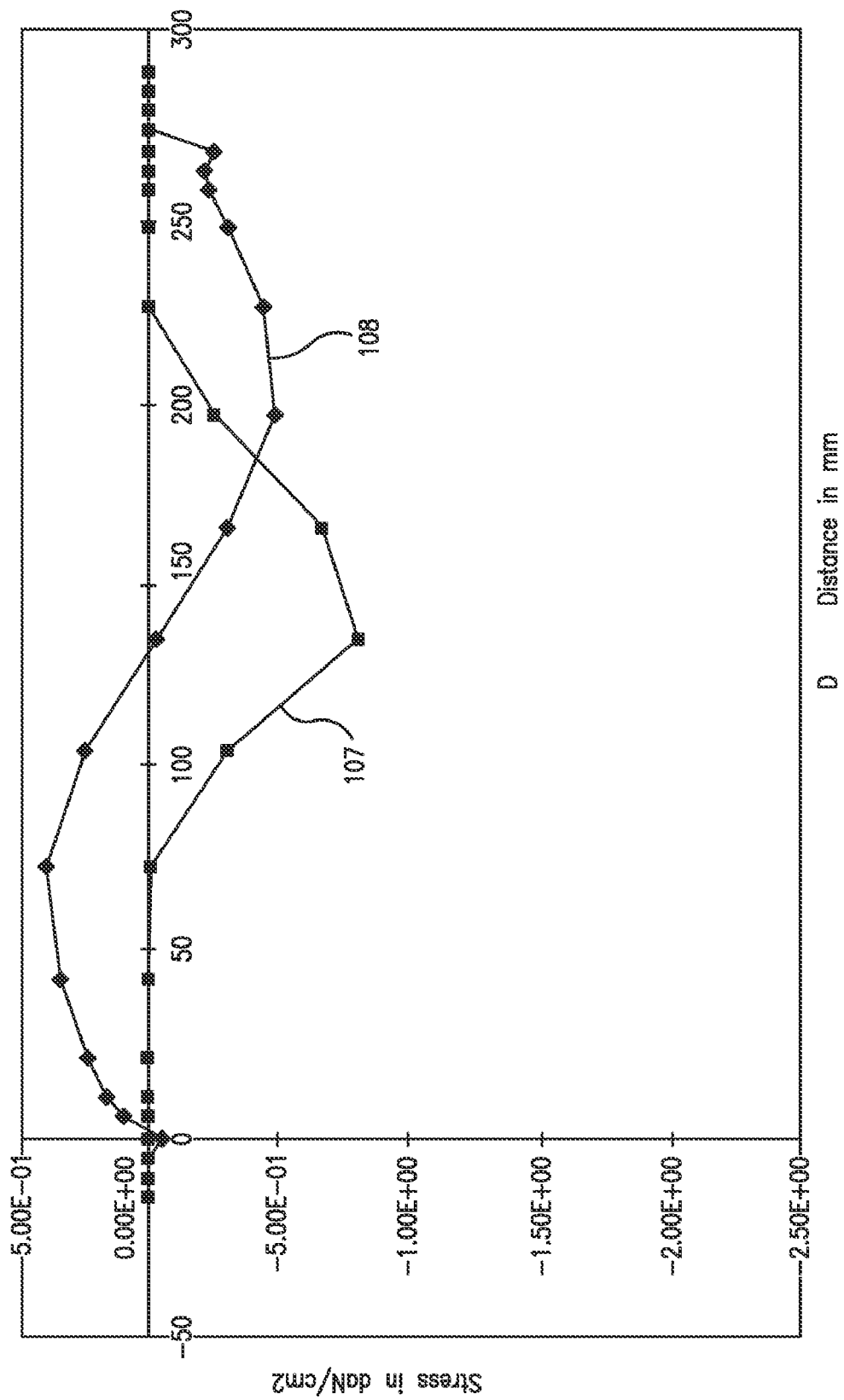
FIG. 20 is a graphical representation of the observations proposed by the invention in a non-idealized case.

If the friction potential is not infinite, which is the case in reality, the point in question will slide on the road surface as soon as the shear stress reaches the maximum value permitted by the friction potential. For a more realistic case in which the friction potential equals 0.5, FIG. 20 shows the longitudinal stresses (in daN/cm$^2$) on a sacrificed rib 101 (curve 107) and an ordinary rib 102 (curve 108) adjacent thereto, in the area of contact, as a function of the distance D (in mm) between the edge of the contact area and the point considered. The signal representing the shear stress as a function of the distance traveled by the center of the wheel is different from that shown in FIG. 19. The form of the signal, and more particularly its maximum value, is directly related to the friction potential.

If the friction potential changes or evolves, the initial part of the stress signal shown as a function of the distance traveled (equal to the speed multiplied by the time that has passed since the instant of first contact with the road) changes only very little. In contrast, the final part of the signal is modified in proportion to the friction potential level. Thus, analysis of the shear stress signal exerted on the sacrificed rib 101 gives information about the friction potential between the rib 101 and the road, which is itself directly correlated to the adherence potential of the tire on the road.

From a pre-established relation connecting the friction potential of the rib and the adherence potential of the tire, on the one hand, and a regular re-calibration procedure, using for example the property by virtue of which the maximum adherence potential of the tire under all road conditions taken together does not change very much, it is possible to deduce the value of the tire's adherence potential from the value of the shear stress exerted on the sacrificed rib, or that of any signal representing such shear stress. This re-calibration procedure is necessary because the pressure under the sacrificed rib can change progressively as the tire becomes worn, for example as a friction of tire wear, even under identical conditions of tire load and inflation pressure, and this pressure evolution introduces a variable which modifies the relationship between the shear stress exerted on the rib and the tire's adherence potential.

If the sacrificed rib is additionally equipped to measure the vertical stress at the same point, the coefficient of friction between the rib and the ground can be calculated by finding the ratio between the shear stress and the vertical stress. In that case, there is no longer any need to re-calibrate regularly in order to evaluate the tire's adherence potential.

Accordingly, in an advantageous embodiment of the detection method, the steps required for the detection of a variation of a first signal, representing the shear stress, and for producing an estimate of the adherence potential within the tire contact area, comprise the following:

(a) generating of a second signal representing a vertical force in the contact surface of the first measuring element;

(b) generating from the first and second signals a third signal representing the ratio between the tangential force and the vertical force;

(c) detecting a variation of the third signal that characterizes a loss of adherence;

(d) producing an estimate of the friction potential in the contact surface of the first measuring element; and (e) from the friction potential, producing an estimate of the adherence potential in the tire contact surface.

The braking stress that develops in the contact area results from the radial difference between the outer circumferences of the sacrificed rib 111 and the adjacent ribs 102. Thus, by modifying this radial difference, the rapidity with which the stress increases between the instants of entry into contact and exit therefrom is changed: the larger the length difference, the more rapidly the shear stress increases.

If the tire is rolling with a sideways drift angle, a transverse stress develops at the interface between the sacrificed rib and the road. This is vectorially added to the longitudinal stress. The resultant then undergoes the same evolution as that described earlier, namely in that its modulus increases between the instant when contact is established and the instant when its value reaches the maximum permitted by the friction potential, provided that the difference between the lengths of the circumferences of the sacrificed rib and the adjacent ribs is sufficiently large.

Figure 21:
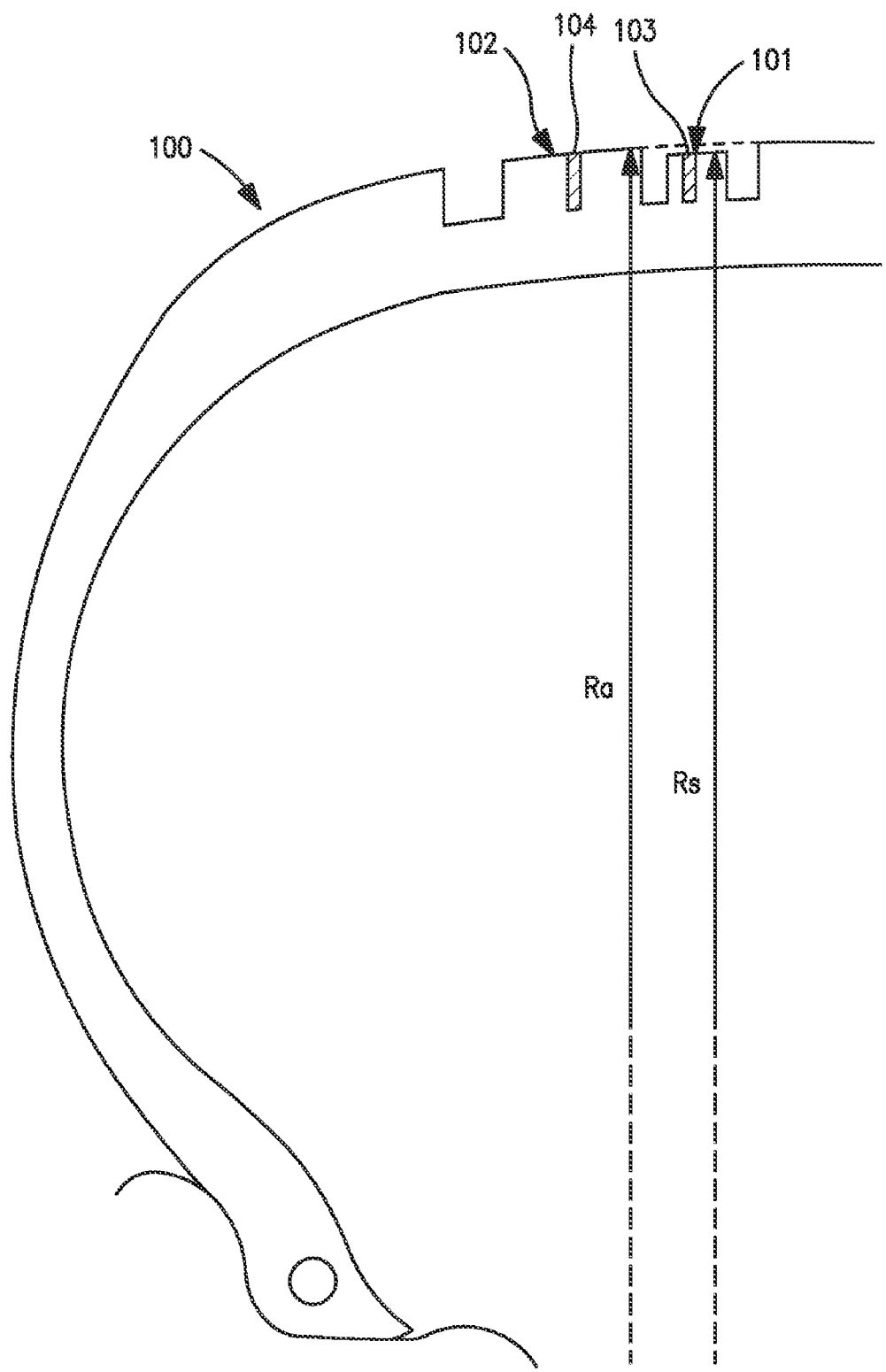
FIG. 21 is a radial section of a tire according to still another embodiment of the invention.

In another advantageous embodiment of the method, one or more sensors 104 may be provided in an ordinary rib, tread block or second tread element 102 (see FIG. 21). This enables the measurement of the deformations or stresses to which the rib or tread block 102 is subjected, while the tire is rolling, these being measured in the longitudinal and transverse directions. In this embodiment, the following steps are also included:

(a) producing a first operational tread signal representing a tangential force in a contact surface zone of at least one second element;

(b) producing a second operational tread signal representing a vertical force in the contact surface zone of the at least one second element;

(c) producing an indication characterizing the tangential force exerted on the tire, by integration of the first operational tread signal between the instants when contact between the road and the contact zone begins and ends, across the width of the tire;

(d) producing an indication characterizing the vertical force exerted on the tire, by integration of the second operational tread signal between the instants when contact between the road and the contact zone begins and ends, across the width of the tire; and (e) determining the available adherence margin from the difference between the tire's adherence potential and the ratio between the tangential and vertical forces exerted on the tire.

This way of estimating the available adherence margin entails estimating the vertical and tangential forces in the elements of the tread. Below, another method is explained which dispenses with that knowledge or these estimates.

Figure 22:
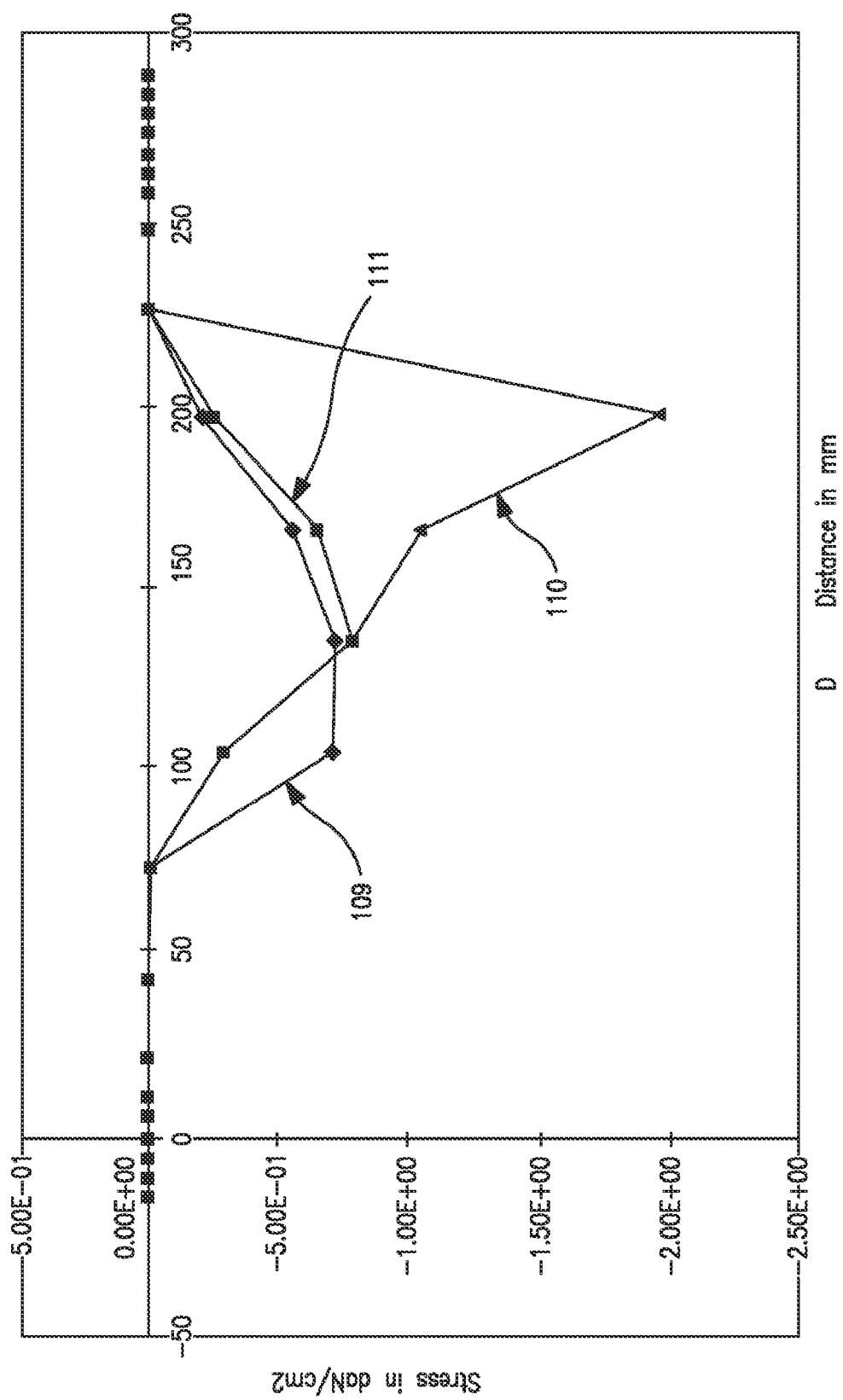
FIG. 22 is a graphical representation showing other observations proposed by the invention.

FIG. 22 shows the longitudinal shear stresses (in daN/cm$^2$) in a sacrificed rib, in the area of contact, as a function of the distance D (in mm) between the edge of the contact zone and the point considered, (i) in the case of rolling with a braking couple and a friction potential equal to 0.5 (curve 109), (ii) in the case of free rolling and infinite friction potential (curve 110), and (iii) in the case of free rolling and a friction potential equal to 0.5 (curve 111). If a drive or braking couple is exerted on the tire, a longitudinal stress is added to or subtracted from the stress induced by the length difference between the circumferences of the ribs. In the case of a braking couple, for example, the stress signal increases more rapidly as a function of the distance traveled than in the case when the wheel is running with no couple acting on it. (Compare curve 109 with curves 10 and 111 in FIG. 22.)

Figure 23:
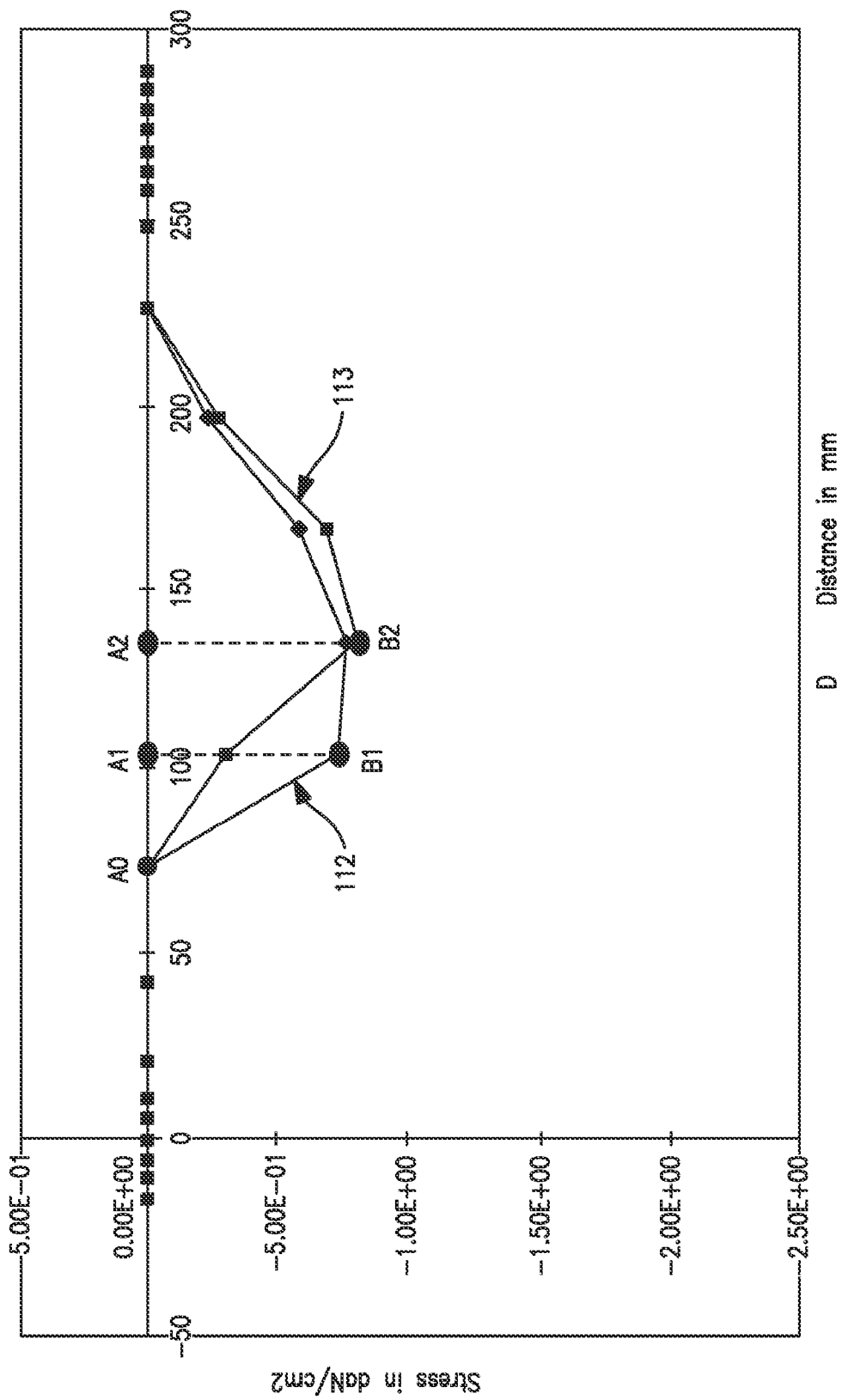
FIG. 23 is a graphical representation showing still other observations proposed by the invention.

FIG. 23 shows plots of signals representing the longitudinal shear stresses (in daN/cm$^2$) as a function of the distance D (in mm) between the edge of the contact zone and the point considered, developed under a sacrificed rib and along given ground, in the case when a braking couple is applied (curve 112), on the one hand, and during free rolling (curve 113), on the other hand. The points B1 and B2 are the points of the curves that correspond to an abrupt variation in the slopes of the curves. This abrupt variation represents a loss of adherence (beginning of sliding) or a restoration of adherence (end of sliding). The point A0 corresponds to the beginning of the contact zone. It can be seen from FIG. 23 that the mean gradient of curve 112 between points A0 and B1 is steeper in its absolute value than that of curve 113 between the points A0 and B2. This is because the available adherence margin in the case corresponding to curve 112 is smaller than the available adherence margin in the case corresponding to curve 113. The ratio between the mean gradient and the value of the signal at the point characterizing a loss of adherence (respectively B1 and B2 on curves 112 and 113) is an example of an indicator of the available adherence margin.

Accordingly, in a particular application of the method intended to produce an indication of the available adherence margin without having to measure or estimate the vertical and tangential forces effectively acting on the tire, the invention proposes that the friction of the shear stress signal should be the ratio between the mean value of the first derivative of that signal relative to the time and value of the signal at the point that characterizes a loss of grip.

Considered in another way, it can be seen that the length of the segment A0-A1 is smaller than that of the segment A0-A2. This expresses the fact that the available adherence margin in the case of curve 112, corresponding to the braking couple, is smaller than the available adherence margin in the case of curve 113 corresponding to free rolling. Thus, the lengths of these segments provide further information representing the available adherence margin, since such margin decreases as the length of the segments becomes shorter.

Accordingly, in a particular application of the method intended to produce an indication of the available adherence margin without having to measure or estimate the vertical and tangential forces effectively acting on the tire, the invention proposes that the function of the signal should be the time interval separating the detections.

Thus, from an appropriate analysis of the stress signal represented as a function of the distance traveled, equal to the product of the speed and the time passing since the entry of the point where the measurement is effected into contact with the ground, information of two kinds can be obtained: (1) information representing the adherence potential between the tire and the road, and (2) information about the level of constraint (drive power, braking or transverse movement) exerted on the tire, from which, therefore, the tire's available adherence margin can be determined.

Measurements of the longitudinal and transverse deformations of the rib can be used in the same way instead of measurements of the stresses. Simply, when it is desired to calculate the coefficient of friction, a prior correlation between the values of the deformations and stresses must be established and taken into account in the calculation.

All that has been described above for a sacrificed rib can also be applied in the case of the measuring elements of the embodiments of FIGS. 1-16.

With certain tires, if the sacrificed rib or tread block is made from the same material as the adjacent ribs or tread blocks, it can be difficult to produce under the sacrificed rib or tread block a shear stress sufficiently high to cause the rib to slide on any type of ground surface and from the free rolling of the tire. During the wear of the tire, the vertical contact pressure between the sacrificed ribs or tread bocks and the ground may become very small because the initial wear of the sacrificed ribs or tread blocks is more rapid than the wear of the tire's other ribs or tread blocks. This can have an adverse effect on the precision with which the adherence potentials are determined when the sacrificed ribs or tread bocks have reached a condition of wear in which the contact pressure is very low.

It is known that, disregarding the groove effect due to the tread pattern, the pressure exerted on the ground in the contact area corresponds essentially to the nominal inflation pressure of the tire. Now, by its very nature, the pressure under a sacrificed rib or tread block is only a fraction of the nominal inflation pressure. To be specific, it has been observed experimentally that the measurements proposed by the present invention give reliable results if the residual ground-contact pressure under the sacrificed rib or tread block (or more generally, the first measuring element) preferably amounts to at least 30% to 40% (and better still, at least 50%) of the nominal pressure.

During free rolling, and because of the phenomenon of rubber wear, an equilibrium is established such that the wear rates of the sacrificed element (rib or tread bock) and the ordinary tread elements (rib or tread blocks) are identical, so that the difference in height between the sacrificed and other elements is constant. At this equilibrium, a certain residual pressure is found under the sacrificed element. If this residual pressure is too small (for example 10% of the nominal pressure), the measurements described in the present application cannot be made, or at least such measurements are not reliable because they are not representative of the adherence prevailing under the ordinary elements (i.e. the non-sacrificed elements) of the tread. Accordingly, it is proposed to use for the sacrificed element a modified material, so that the residual pressure will be sufficiently high. It has been verified experimentally that the measurement conditions are much better and the results are sufficiently representative of the adherence conditions prevailing for unmodified materials.

Thus, in another embodiment of the present invention, the sacrificed element (see rib 101 in FIG. 17) is made of a material different from that used to make the ordinary element, such that the sacrificed element has better wear resistance than the ordinary elements. In this way, despite the fact that by the nature of the invention the sacrificed element is subjected to stresses prejudicial to its longevity, the sacrificed element is kept in a condition appropriate for the estimation of the adherence potential or adherence margin.

In another embodiment of a tire according to the invention, the sacrificed element (see rib 101 in FIG. 17) is made of a material different from the material used to make the ordinary elements, such that the sacrificed element has an adherence potential lower than the ordinary elements. This has the advantage that the tangential stresses required to produce sliding of the sacrificed element are reduced.

For example, at the tire production stage a tread can be made by co-extrusion of different uncured rubbers appropriate for the purpose. The point of this measure is to allow the sacrificed elements to slide, against a given ground surface, at shear stresses lower than those that would be necessary if these elements consisted of the same materials as that of the tire's ordinary tread blocks or ribs. Since the wear rate of a rubber element decreases very rapidly with decreasing shear stress between the contact area of the element and the ground, when the element slips along the ground, the consequence of this improvement is that the sacrificed ribs or tread blocks made from a material with less adherence will wear away less quickly, and the vertical contact pressure between the sacrificed ribs or tread blocks and the ground will also decrease less quickly during the wear of the tire.

Still another embodiment according to the invention concerns a tire in which the sacrificed element is made of a material with higher Young's modulus than that of the material used for the ordinary elements. The consequence of this is to increase the tangential stresses at the moment when sliding begins. This measure can be combined with the previous one.

For this reason, it is also proposed in another advantageous embodiment to make the sacrificed ribs or tread blocks of a material with better wear resistance than the material constituting the other ribs or tread blocks of the tire's tread pattern. The point of this measure is again to reduce the wear rate of the sacrificed ribs or tread blocks, and consequently to achieve a less rapid decrease of the vertical contact pressure of the sacrificed elements during the wear of the tire.

The foregoing three concepts can be advantageously combined. Such a combination makes it possible throughout the life of the tire to maintain a vertical contact pressure between the sacrificial ribs or tread blocks and the ground, which is sufficiently high to ensure good precision of the adherence potential measurements.

The tire's adherence potential on the road directly determines the maximum level of the steering, braking and drive-power forces that can be transmitted to the vehicle. It is a determinant factor of the vehicle's mobility and road-holding.

Statistical studies carried out in several countries show that there is indisputably a relation between the adherence potential and the risk of accidents on wet roads: namely, the lower the adherence potential on a wet road, the higher the risk of an accident. Thus, the safety of users is closely dependent on the potential.

An important contribution to safety is to be able to evaluate the level of the adherence potential of a tire as early as possible before it reaches its adherence limit, since the possibility of avoiding an accident in the case of insufficient adherence will be the greater, the sooner action is taken to adapt the rolling conditions of the vehicle.

The design principle of a tire according to the present invention offers considerable advantage from this standpoint. In effect, it enables the level of the adherence potential to be evaluated even when the tire is rolling freely, which amounts to saying that the adherence potential can be determined under any vehicle rolling conditions, from the situation of rolling in a straight line at constant speed to situations of maximum braking and acceleration, or going around bends at the very limit of adherence. Thus, the available adherence potential can be evaluated continuously.

From the same measurements it is also possible to know what fraction of the adherence potential is effectively being utilized.

The table below shows the applications permitted by knowledge of such information.

| | RECIPIENT OF THE INFORMATION | | |
|---|---|---|---|
| INFORMATION RECORDED | DRIVER | VEHICLE | OTHER USERS AND ROAD MANAGERS |
| Adherence potential | Inform of the variations in limit of adherence potential Compare the momentary potential | Adapt the control strategy of active systems (anti-locking, antiskid, path monitoring) | Inform other users of the available adherence level at all points of the network (in combination with a |

-continued

| | RECIPIENT OF THE INFORMATION | | |
|---|---|---|---|
| INFORMATION RECORDED | DRIVER | VEHICLE | OTHER USERS AND ROAD MANAGERS |
| | with a statistical population of the adherence levels and inform of the position of this momentary potential compared with this population (high, average, weak, very weak level) | Assist the driver, correct actions when the latter seem unsuitable or when corrective action seems necessary given the expected response of the vehicle | position tracking system) Supply the bodies responsible for the upkeep of the network with real time data permitting optimum management of the upkeep |
| Available adherence margin | Inform the driver of the level of use of the potential and alert him to the approach of the adherence limit | Regulate active systems (antilocking, antiskid, path monitoring) | Alert managers of the road networks to areas where the adherence limit is most often approached |

Based solely on a knowledge of the available adherence potential, or of information directly related to the adherence potential, it is possible:

to inform the driver of the vehicle:

(a) when variations in the adherence level occur: for example, if the potential declines beyond a certain variation limit, an alert may be supplied to the driver in audible or visual form to encourage him to adapt his driving and to increase his vigilance; and (b) of the relative adherence level which is available to him at a given moment compared with a statistical base of the adherence limits encountered: the information sampled continuously, when the vehicle is rolling, may supply a data base implanted in a computer system connected to the vehicle or external to the vehicle (centralized data base with which the vehicle would communicate); in addition, the information may be compared with the statistical population already stored in the data base in order to determine the percentile of the population to which it corresponds; the result may be converted into a single item of information supplied to the driver (for example, by the indication of an agreed level describing the available adherence: high, average, weak, very weak);

to act on the vehicle:

(a) by adapting the control strategies of systems of the vehicle such as the wheel antilocking, antiskid and active path monitoring systems: the systems could possess strategies differing according to the adherence level and predefined by construction; depending on the momentary adherence level, the most suitable control strategy could be implemented; and (b) by permitting the determination of the optimal actions to be applied to a component of the vehicle: numerical simulations in real time can now be carried out in the vehicles; with a knowledge of the adherence level, it is possible to establish the action to be applied to a component (for example, the brakes) in order that the response is optimal; it is also possible to predict by simulation what will be the response of the vehicle to the actions performed by the driver and to consequently correct his actions or to assist him should the actions appear unsuitable;

to inform other road users and bodies responsible for the upkeep of the road network, by communicating said information to central data bases; the current means of communication and location of the mobiles (GPS system for example) make it possible to assign to each item of information concerning the adherence potential supplied by a vehicle, the precise location of the corresponding portion of road, and to transmit this information to a centralized system; on the basis of this information, it is possible:

(a) to inform other users of the road, and their vehicles, of the level available at a given point even before they have reached that point, which makes it possible to anticipate to an even greater extent any corrective measures required in terms of the controls of the vehicles; and (b) to supply the managers of the road network with accurate statistical information in real time on the adherence level, thus rendering superfluous the regular operations to measure the adherence which are carried out in certain countries in order to monitor their road network, If this information on the available adherence potential is complemented with the information on the adherence level actually used, it is possible in addition:

to inform the driver of the rate of use of the available adherence potential and to alert him to the approach of the adherence limit;

to regulate systems of the vehicle (wheel antilocking and antiskid systems, for example) directly from the difference between the available potential and the potential used; and to supply the persons responsible for managing the road network with statistical information enabling them to detect the points of the network where the adherence limit is most often approached and where the risk of an accident may consequently be considerable, even before this risk is highlighted by accident statistics.

The measurements described above in connection with FIGS. 1-23 may be carried out in any conventional manner. For example, the measurement apparatus disclosed in German Offenlegungsschrift DE 39 37 966 A1 may be used for that purpose. In pertinent part, that apparatus is illustrated in FIGS. 24-27 hereof.

Figure 24:
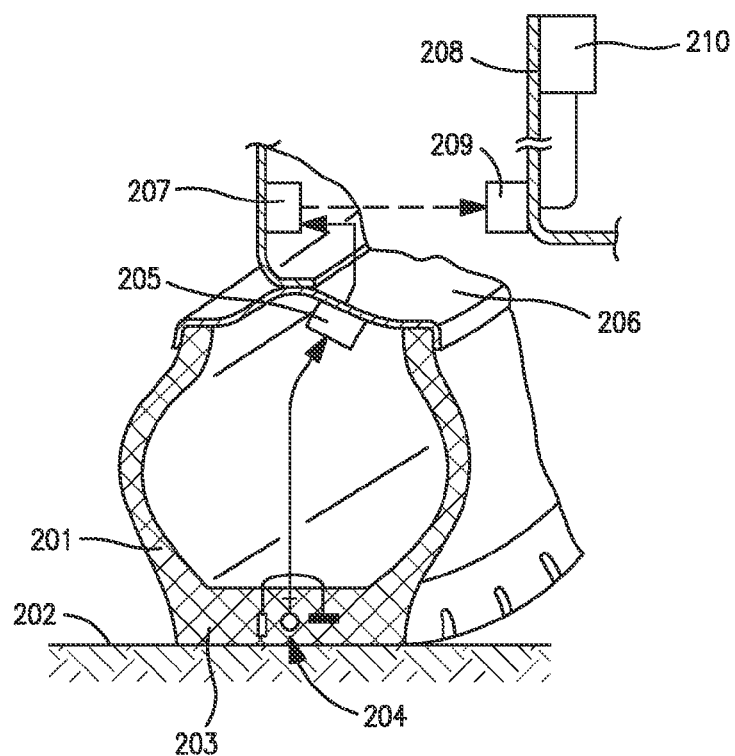
FIGS. 24-27 are schematic representations of a known apparatus for generating measurement and output signals in accordance with the invention.

The apparatus, shown schematically in FIG. 24, for determining the conditions of dynamic engagement between a vehicle tire 201 and a roadway 202, includes a sensor 204 provided within a tread block or rib of the tread 203. The sensor 204 detects the local stresses in circumferential, transverse and perpendicular directions as a function of time at a point of measurement in the tire contact zone or area, while this point passes through the tire contact zone as the tire 201 rolls along the roadway 202. The signals supplied by the sensor 204 are passed to an amplifier 205 at the rim 206 of the vehicle wheel, and thence to a signal transmitter 207 likewise attached to the rim 206. This signal transmitter 207 forwards the signals electrically to a signal receiver 209 mounted on the vehicle superstructure 208. This transmission may be contactless, for example inductive or by way of a frequency-modulated signal, or else by way of slip rings. The signal receiver 209 passes the measurement signals to an evaluating means 210, which may be a suitably programmed microprocessor. In the evaluating means 210, the measurement signals as functions of time are processed to determine the adherence potential, the friction potential and/or the available adherence margin according to one or more of the methods described above. The signal processing steps are very straightforward and well within the capabilities of readily available microprocessors and application programs. Thus, they are not further described herein.

Figure 25:
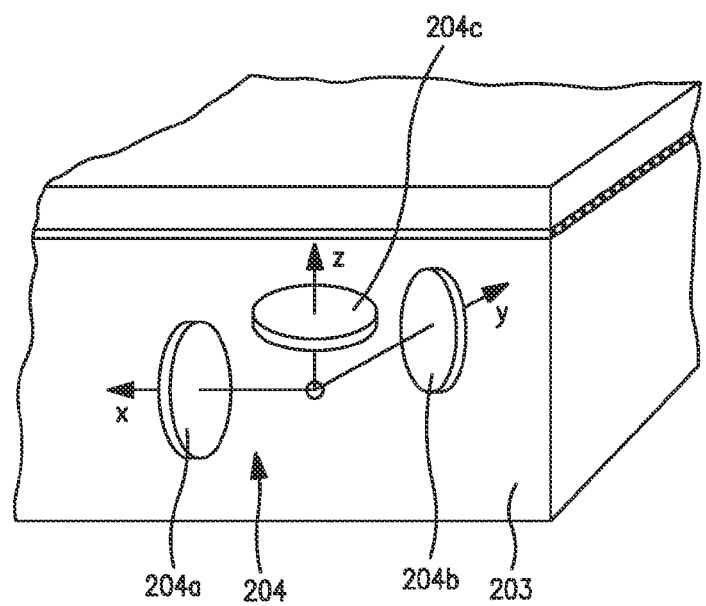

FIG. 25 shows, schematically, the arrangement of three piezoelectric transmitters 204a, 204b and 204c forming the sensor 204 in FIG. 24. The transmitter 204a detects the stresses, or strains or deformations in the x-direction, i.e. in circumferential direction of the tire; the transmitter 204b detects the stresses, or strains or deformations in the y-direction, i.e. in transverse direction, and the transmitter 204c detects the stresses, or strains or deformations in the z-direction, i.e. perpendicularly.

Figure 26:
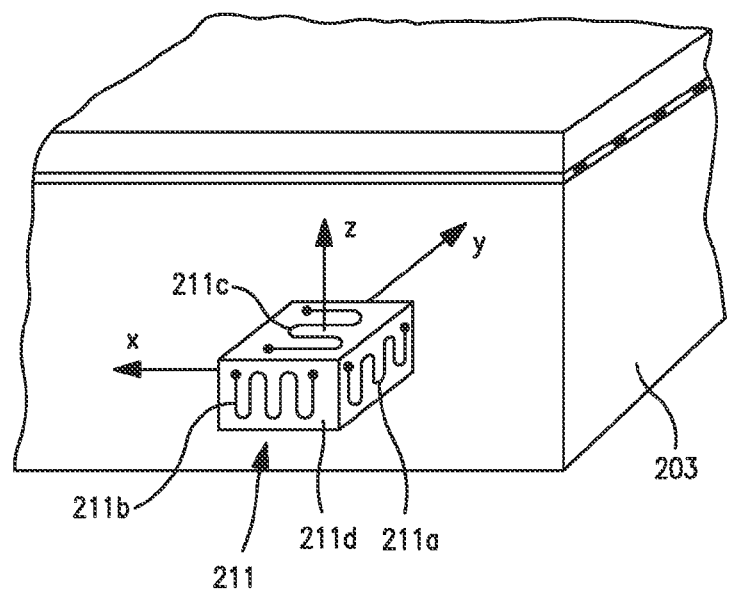

The sensor 211 shown schematically in FIG. 26, which may be used instead of the sensor 204 of FIG. 24, and which is likewise embedded in the tread 203 of the tire, comprises a deformation member 211d fitted with extensimeter strips 211a, 211b, 211c. In the embodiment shown, by way of example, the deformation member 211d is an elastically deformable chamber whose walls bear the extensimeter strips 211a, 211b and 211c. Like the piezoelectric transmitters 204a, 204b and 204c of FIG. 25, the extensimeter strips 211a, 211b and 211c of FIG. 26 are so arranged that they have different directions of action, preferably located on the mutually perpendicular axes x, y and z.

Figure 27:
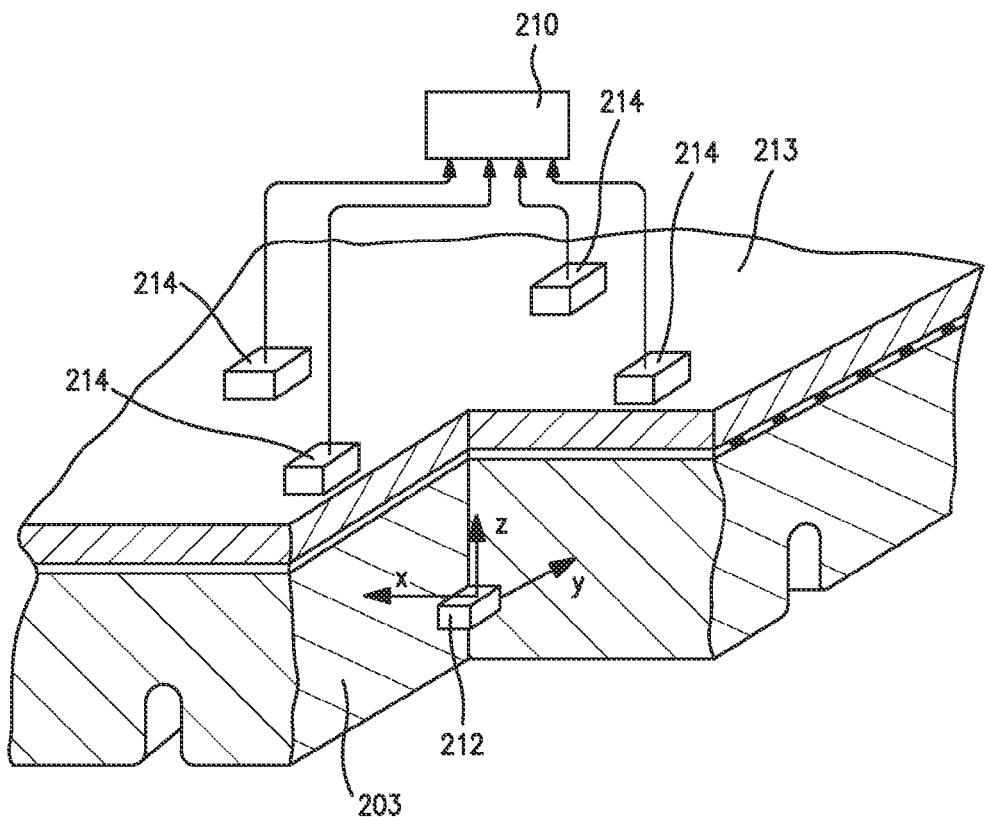

Another sensor structure is shown in FIG. 27. A permanent magnet 212 is imbedded in the tread 203 as a transmitter, its position varying according to the deformations that occur. On the inside 213 of the tire, as receivers, for example, are arranged four Hall generators 214, responding to variations in distance from the transmitter 212. The measurement signals of the Hall generators 214, in the evaluating means 210, deliver information concerning variations in the spatial position of the transmitter 212, due to the occurrence of local strains or deformations in the tire profile. Thence the local stresses and, hence, the momentarily utilized and maximum adherence potential can be determined. In this arrangement, transmitter and receiver may alternatively be interchanged.

As an alternative to the detection apparatus of DE 39 37 966, the measurements could be performed using the apparatus disclosed in U.S. Pat. No. 5,864,056, No. 5,502,433 and No. 5,913,240, the disclosures of which are hereby incorporated by reference for all purposes. As before, the measurement signals would be transmitted to a suitably programmed microprocessor or other evaluation means for determination of the adherence potential, the friction potential and/or the available adherence margin as described above.

These calculated items of information are themselves addressed, for example, to a device enabling the driver to be informed, or else are sent, for example by radio means, to a system external to the vehicle allowing centralization of the information relating to the adherence potential with the ground and designed to notify all road users, or else again are used to regulate systems or components of the vehicle to which the tire is fitted.

What is claimed is:

1. A method for the detection of an adherence characteristic between a tire with a deformable tread and a surface along which it is rolling, comprising the steps of:
   a) providing in the tread at least one first measuring element and at least one second element, each said tread element having a contact surface with the ground, the contact surface of the first measuring element being configured such that, during normal operation of a vehicle wheel equipped with the tire, the surfaces of the first and second elements come into contact with the ground on each revolution of the tire and, at least within a range of rolling conditions to be monitored, the contact surface of the first element slides relative to the ground during its passage through the contact area;
   b) generating a first signal that represents a tangential force in the contact surface of the first measuring element;
   c) detecting a variation of the first signal that characterizes a loss of adherence;
   d) producing an estimate of the friction potential in the contact surface of the first measuring element; and
   e) producing an estimate of adherence potential of the tire.

2. A method according to claim 1, in which:
   step c) comprises
   1) generating a second signal representing a vertical force in the contact surface of the first measuring element;
   2) producing from the first and second signals a third signal representing the ratio between the tangential and vertical forces; and
   3) detecting a variation of the third signal that characterizes a loss of adherence;
   step d) comprises producing an estimate of the friction potential based upon the detection of step c) 3); and
   step e) comprises producing an estimate of the adherence potential based upon the frictional potential estimated in step d).

3. A method according to claim 1, further comprising the steps of:
   f) generating a first operational tread signal representing a tangential force in a zone of the contact surface of the at least one second element;
   g) generating a second operational tread signal representing a vertical force in a zone of the contact surface of the at least one second element;
   h) producing an indication that characterizes the tangential force applied to the tire, by integration of the first operational tread signal between the instants when the contact of said zone with the ground begins and ends, and across the full width of the tire;
   i) producing an indication that characterizes the vertical force applied to the tire, by integration of the second operational tread signal between the instants when the contact of said zone with the ground begins and ends, and across the full width of the tire; and
   j) determining the available adherence margin as the difference between the tire's adherence potential and the ratio between the tangential and vertical forces applied to the tire.

4. A method for detecting an adherence characteristic between a tire with a deformable tread and a surface over which it is rolling, comprising the steps of:
   a) providing in the tread at least one first measuring element and at least one second element, each said tread element having a contact surface with the ground, the contact surface of the first tread element being configured such that, during normal operation of a vehicle wheel equipped with the tire, the surfaces of the first and second elements come into contact with the ground on each revolution of the tire and, at least within a range of rolling conditions to be monitored, the contact surface of the first measuring element slides relative to the ground during its passage through the contact area;

b) generating a first signal representing a tangential force in the zone of the contact surface of the first measuring element;

c) detecting in the first signal the instant when the first measuring element enters the contact area;

d) detecting in the first signal the instant when the first signal undergoes a variation that characterizes a loss of adherence; and e) producing an indication that characterizes an available adherence margin from a function of the first signal between the instant when entry into the contact area is detected and the instant when said characteristic variation is detected.

5. A method according to claim 4, in which the function of the first signal is the ratio between the mean value of the first derivative of the first signal relative to the time and the value of the first signal at the instant that characterizes the loss of adherence.

6. A detection method according to claim 4, in which the function of the first signal is the time interval separating said detections of steps c) and d).

7. A method according to claim 1, wherein:
   a) the first measuring element of step a), viewed at the surface of the tread, has a central zone surrounded by an encircling zone, the central zone being arranged to slide over the ground with a level of stress parallel to the surface of the ground which is substantially weaker than the level of stress parallel to the surface of the ground beyond which the encircling zone will slide over the ground; and
   b) the sensor of step b) is arranged to achieve a measurement in the central zone, the sensor being sensitive to at least one parameter reflecting a tangential force exerted at the surface of the central zone.

8. A method according to claim 1, wherein the contact surface of the first measuring element is located at a distance from the wheel axle that is less than the distance of the contact surface of the second tread element from the wheel axle.

9. A method according to claim 2, further comprising the steps of:
   f) generating a first operational tread signal representing a tangential force in a zone of the contact surface of the at least one second element;
   g) generating a second operational tread signal representing a vertical force in a zone of the contact surface of the at least one second element;
   h) producing an indication that characterizes the tangential force applied to the tire, by integration of the first operational tread signal between the instants when the contact of said zone with the ground begins and ends, and across the full width of the tire;
   i) producing an indication that characterizes the vertical force applied to the tire, by integration of the second operational tread signal between the instants when the contact of said zone with the ground begins and ends, and across the full width of the tire; and
   j) determining the available adherence margin as the difference between the tire's adherence potential and the ratio between the tangential and vertical forces applied to the tire.

10. A method according to claim 4, wherein:
    a) the first measuring element of step a), viewed at the surface of the tread, has a central zone surrounded by an encircling zone, the central zone being arranged to slide over the ground with a level of stress parallel to the surface of the ground which is substantially weaker than the level of stress parallel to the surface of the ground beyond which the encircling zone will slide over the ground; and
    b) the sensor of step b) is arranged to achieve a measurement in the central zone, the sensor being sensitive to at least one parameter reflecting a tangential force exerted at the surface of the central zone.

11. A method according to claim 4, wherein the contact surface of the first measuring element is located at a distance from the wheel axle that is less than the distance of the contact surface of the second tread element from the wheel axle.

* * * * *